US009944937B2

(12) United States Patent
Howard et al.

(10) Patent No.: US 9,944,937 B2
(45) Date of Patent: Apr. 17, 2018

(54) REGULATORY REGION HAVING INCREASED EXPRESSION AND METHOD OF USING SAME

(75) Inventors: John Howard, Cayucos, CA (US); Celine Hayden, San Luis Obispo, CA (US)

(73) Assignee: Applied Biotechnology Institute, Inc., San Luis Obispo, CA (US)

(*) Notice: Subject to any disclaimer, the term of this patent is extended or adjusted under 35 U.S.C. 154(b) by 985 days.

(21) Appl. No.: 13/558,834

(22) Filed: Jul. 26, 2012

(65) Prior Publication Data

US 2013/0031664 A1 Jan. 31, 2013

Related U.S. Application Data

(60) Provisional application No. 61/512,347, filed on Jul. 27, 2011.

(51) Int. Cl.
*C12N 15/82* (2006.01)
*C12N 15/113* (2010.01)

(52) U.S. Cl.
CPC ........ *C12N 15/8216* (2013.01); *C12N 15/113* (2013.01); *C12N 15/8234* (2013.01)

(58) Field of Classification Search
CPC combination set(s) only.
See application file for complete search history.

(56) References Cited

U.S. PATENT DOCUMENTS

| | | | |
|---|---|---|---|
| 7,112,723 B2 | 9/2006 | Streatfield | |
| 7,169,967 B2 | 1/2007 | Streatfield | |
| RE41,318 E | 5/2010 | Jilka | |
| 2003/0100748 A1* | 5/2003 | Misra et al. | 536/23.6 |
| 2005/0246787 A1* | 11/2005 | Streatfield et al. | 800/278 |
| 2013/0042370 A1 | 2/2013 | Howard et al. | |

FOREIGN PATENT DOCUMENTS

WO WO1998059062 A1 * 12/1998

OTHER PUBLICATIONS

Kim et al. 1994. Plant Molecular Biology, 24:105-117.*
Omirulleh et al. 1993. Activity of a chimeric promoter with the doubled CaMV 35S enhancer element in protoplast-derived cells and transgenic plants in maize. Plant Molecular Biology 21: 415-428.*
Suzuki et al. 2005. Quantitative statistical analysis of cis-regulatory sequences in ABA/VP1- and CBF/DREB1-regulated genes of *Arabidopsis*. Plant physiology 139: 437-447.*

(Continued)

*Primary Examiner* — Ashley K Buran
*Assistant Examiner* — Karen M Redden
(74) *Attorney, Agent, or Firm* — McKee, Voorhees, Sease, PLC

(57) ABSTRACT

An enhanced globulin-1 regulatory region is shown, a nucleotide sequence of which includes at least one additional copy of a region of the globulin-1 regulatory region which includes at least one transcriptional factor binding domain, combined with a transcription initiation site and translation start site. The promoter provides improved seed preferred, and particularly embryo preferred expression in plants. Methods of use are also shown in preferentially expressing a heterologous protein to the embryo tissue of a plant.

5 Claims, 14 Drawing Sheets

(56) References Cited

OTHER PUBLICATIONS

Fang et al. 1989. Multiple cis regulatory elements for maximal expression of the cauliflower mosaic virus 35S promoter in transgenic plants. The Plant Cell 1: 141-150.*
Kay et al. 1987. Cuplication of CaMV 35S promoter sequences creates a strong enhancer for plant genes. Science 236: 1299-1302.*
Liu et al. (1992) MNL vol. 22: 108-109.
Belanger, F.C. and Kriz, A.L. (1991) "Molecular basis for allelic polymorphism of the maize globulin-1 gene" Genetics 129, 863-872.
Kriz (1989) "Characterization of embryo globulins encoded by the maize Glb genes" Biochem Genet. 27(3-4):238-51.
GenBank accession L22344 Aug. 4, 1993.
Veerla et al. (2010) "Genome-wide transcription factor binding site/promoter databases for the analysis of gene sets and co-occurrence of transcription factor binding motifs" BMC Genomics 11:145.
Windenger et al. (1996) "TRANSFAC: a database on transcription factors and their DNA binding sites" Nucleic Acids Research vol. 24, No. 1 pp. 238-241.
Sandelin et al. (2004) "JASPAR: an open-access database for eukaryotic transcription factor binding profiles" Nucleic Acids Research vol. 32, Database issue D91-D94; DOI: 10/1093/nar/gkh012.
Plant promoter and Regulatory Element Resources—DATF: Database of *Arabidopsis* Transcription Factors provided by The *Arabidopsis* Information Resource (TAIR) through the *Arabidopsis* Biological Resource Center at Ohio State University at www.arabidopsis.org/portals/genAnnotation/genome_annotation_tools/cis_element.jsp.
Catharius et al. (2005) Bioinformatics vol. 21 No. 13, pp. 2933-2941.
Hattori et al, (1992) "The Viviparous-1 gene and abscisic acid activate the C1 regulatory gene for anthocyanin biosynthesis during seed maturation in maize"Genes and Development vol. 6, p. 609-618.
Hattori et al, 2002, "Experimentally determined sequence requirment of AcGT-containing abscisic acid response lement" Plant and Cell Physiology, 43(1)p. 136-140.
Hood, et al. (2003) "Criteria for high-level expression of a fungal laccase gene in transgenic maize" Plant Biotechnol. J. 1, 129-140.
Woodard, et al. (2003) "Maize-derived bovine trypsin: characterization of the first large-scale, commercial protein product from transgenic plant". Biotechnol. Appl. Biochem. 38,123-130.
Donaldson et al. (2005) "TFBScluster: a resource for the characterization of transcriptional regulatory networks" Bioinformatics vol. 21 No. 13, pp. 3058-3059.
Chen et al. (2002) "Expression profile matrix of *Arabidopsis* transcription factor genes suggests their putative functions in response to environmental stresses" Plant Cell Vo. 14, 559-574.
Kriz et al. (1986) "Syntehsis of globulins in maize embryos" Plant Physiol. 82, 1069-1075.
Kris et al. (1991) "Characterization of the maize Globulin-2 gene and analysis of two null alleles" Biochem. Gen. vol. 29., Nos. 5/6 pp. 241-254.
Sandelin et al. (2004) "JASPAR: an open-access database for eukaryotic transcription factor binding profiles" Nuc. Acids Res. vol. 32, Database issue D91-D94 DOI: 10.1093/nar/gkh012.
GenBank Accession No. KC771214 submitted Mar. 2013, released Jun. 29, 2013.
Belanger et al. (1989) Molecular Characterization of the major maize embryo globulin encoded by the Glb1 gene Plant Physiol. 91, 636-643.
Hayden et al. Production of highly concentrated, heat-stable hepatitis surface antigen in maize Plant Biotechnology Journal 10, pp. 979-984 (2012).
Streatfield et al. "Identification of maize embryo-preferred promoters suitable for high-level heterologous protein production" GM Crops 1:3, 162-172, May/Jun. 2010.
Wallace et al. "Nucleotide Sequence of a cDNA Clone Corresponding to the Maize Globulin-2 Gene" PLant :Physiol. (1991) 95, 973-975.
Streatfield et al. (2007) Approaches to achieve high-level heterologous protein production in plants. Plant Biotechnology Journal 5:2-15.
Hood et al. Manipulating corn germplasm to increase recombinant protein accumulation. Plant Biotechnol J. Jan. 2012;10(1):20-30. doi: 10.1111/j.1467-7652.2011.00627.x. Epub Jun. 1, 2011.
Hennegan et al (2005) Improvement of human lysozyme expression in transgenic rice grain by combining wheat (*Triticum aestivum*) puroindoline b and rice (*Oryza sativa*) Gt1 promoters and signal peptides. Transgenic Research 14:583-592.
Egelkrout et al. "Cellulase expression using maize embryo promoters suitable for high-level heterologous protein production" American Society of Plant Biologists, ABS #P01055, Jul. 31, 2010.
GenBank Ref No. AR947679.1 Sequence 4 from U.S. Pat. No. 7112723, Oct. 8, 2006.
GenBank Ref No. X53715.1 *Z. mays* mRNA for globulin-2, Dec. 15, 2002.
Egelkrout et al. Enhanced expression levels of cellulase enzymes using multiple transcription units Bioenerg. Res. (2013) 6:699-710.

* cited by examiner atggtccgtcctgtagaaaccccaacccgtgaaatcaaaaaactcgacggcctgtgggcattcagtctggatcgcgaaaactgt
ggaattgatcagcgttggtgggaaagcgcgttacaagaaagccgggcaattgctgtgccaggcagttttaacgatcagttcgcc
gatgcagatattcgtaattatgcgggcaacgtctggtatcagcgcgaagtctttataccgaaaggttgggcaggccagcgtatcgt
gctgcgtttcgatgcggtcactcattacggcaaagtgtgggtcaataatcaggaagtgatggagcatcaggcgcggctatacgcc
atttgaagccgatgtcacgccgtatgttattgccgggaaaagtgtacgtatcaccgtttgtgtgaacaacgaactgaactggcaga
ctatcccgccgggaatggtgattaccgacgaaaacggcaagaaaaagcagtcttacttccatgatttctttaactatgccggaatc
catcgcagcgtaatgctctacaccacgccgaacacctgggtggacgatatcaccgtggtgacgcatgtcgcgcaagactgtaa
ccacgcgtctgttgactgccaggtggtggccaatggtgatgtcagcgttgaactgcgtgatgcggatcaacaggtggttgcaact
ggacaaggcactagcgggactttgcaagtggtgaatccgcaccctctgccaaccgggtgaaggttatctctatgaactgtgcgtca
cagccaaaagccagacagagtgtgatatctacccgcttcgcgtcggcatccggtcagtggcagtgaagggccaacagttcctg
attaaccacaaaccgttctactttactggctttggtcgtcatgaagatgcggacttacgtggcaaaggattcgataacgtgctgatg
gtgcacgaccacgcattaatggactggattggggccaactcctaccgtaccctcgcattacccttacgctgaagagatgctcgact
gggcagatgaacatggcatcgtggtgattgatgaaactgctgctgtcggctttaacctctctttaggcattggtttcgaagcgggca
acaagccgaaagaactgtacagcgaagaggcagtcaacggggaaactcagcaagcgcacttacaggcgattaaagagctga
tagcgcgtgacaaaaaccacccaagcgtggtgatgtggagtattgccaacgaaccggatacccgtccgcaagtgcacgggaa
tatttcgccactggcggaagcaacgcgtaaactcgacccgacgcgtccgatcacctgcgtcaatgtaatgttctgcgacgctcac
accgataccatcagcgatctctttgatgtgctgtgcctgaaccgttattacggatggtatgtccaaagcggcgatttggaaacggc
agagaaggtactggaaaaagaactctctggcctggcaggagaaactgcatcagccgattatcatcaccgaatacgccgtggata
cgttagccgggctgcactcaatgtacaccgacatgtggagtgaagagtatcagtgtgcatggctggatatgtatcaccgcgtcttt
gatcgcgtcagcgccgtcgtcggtgaacaggtatggaatttcgccgatttgccgacctcgcaaggcatattgcgcgttggcggta
acaagaaagggatcttcactcgcgaccgcaaaccgaagtcggcgcgttttctgctgcaaaaacgctggactggcatgaacttcg
gtgaaaaaccgcagcagggaggcaaacaacaccatcaccatcaccat

Figure 1A

MVRPVETPTREIKKLDGLWAFSLDRENCGIDQRWWESAL
QESRAIAVPGSFNDQFADADIRNYAGNVWYQREVFIPKG
WAGQRIVLRFDAVTHYGKVWVNNQEVMEHQGGYTPFEA
DVTPYVIAGKSVRITCVNNELNWQTIPPGMVITDENGKK
KQSYFHDFFNYAGIHRSVMLYTTPNTWVDDITVVTHVAQ
DCNHASVDCQVVANGDVSVELRDADQQVVATGQGTSGT
LQVVNPHLCQPGEGYLYELCVTAKSQTECDIYPLRVGIRS
VAVKGQQFLINHKPFYFTGFGRHEDADLRGKGFDNVLMV
HDHALMDWIGANSYRTSHYPYAEEMLDWADEHGIVVIDE
TAAVGFNLSLGIGFEAGNKPKELYSEEAVNGETQQAHLQ
AIKELIARDKNHPSVVMWSIANEPDTRPQVHGNISPLAEA
TRKLDPTRPITCVNVMFCDAHTDTISDLFDVLCLNRYYG
WYVQSGDLETAEKVLEKELLAWQEKLHQPIIITEYGVDTL
AGLHSMYTDMWSEEYQCAWLDMYHRVFDRVSAVVGEQ
VWNFADFATSQGILRVGGNKKGIFTRDRKPKSAAFLLQK
RWTGMNFGEKPQQGGKQHHHHHH

Figure 1B

```
   1 aagcttgccg agtgccatcc ttggacactc gataaagtat attttatttt ttttattttg
  61 ccaaccaaac tttttgtggt atgttcctac actatgtaga tctacatgta ccattttggc
 121 acaattacat atttacaaaa atgttttcta taaatattag atttagttcg tttatttgaa
 181 tttcttcgga aaattcacat ttaaactgca agtcactcga aacatggaaa accgtgcatg
 241 caaaataaat gatatgcatg ttatctagca caagttacga ccgatttcag aagcagacca
 301 gaatcttcaa gcaccatgct cactaaacat gaccgtgaac ttgttatcta gttgtttaaa
 361 aattgtataa aacacaaata aagtcagaaa ttaatgaaac ttgtccacat gtcatgatat
 421 catatataga ggttgtgata aaaatttgat aatgtttcgg taaagttgtg acgtactatg
 481 tgtagaaacc taagtgacct acacataaaa tcatagagtt tcaatgtagt tcactcgaca
 541 aagactttgt caagtgtccg ataaaaagta ctcgacaaag aagccgttgt cgatgtactg
 601 ttcgtcgaga tctctttgtc gagtgtcaca ctaggcaaag tctttacgga gtgtttttca
 661 ggctttgaca ctcggcaaag cgctcgattc cagtagtgac agtaatttgc atcaaaaata
 721 gctgagagat ttaggccccg tttcaatctc acgggataaa gtttagcttc ctgctaaact
 781 ttagctatat gaattgaagt gctaaagttt agtttcaatt accaccatta gctctcctgt
 841 ttagattaca aatggctaaa agtagctaaa aaatagctgc taaagtttat ctcgcgagat
 901 tgaaacaggg ccttaaaatg agtcaactaa tagaccaact aattattagc tattagtcgt
 961 tagcttcttt aatctaagct aaaaccaact aatagcttat ttgttgaatt acaattagct
1021 caacggaatt ctctgttttt ctaaaaaaaa actgcccctc tcttacagca aattgtccgc
1081 tgcccgtcgt ccagatacaa tgaacgtacc tagtaggaac tcttttacac gctcggtcgc
1141 tcgccgcgga tcggagtccc cggaacacga caccactgtg gaacacgaca aagtctgctc
1201 agaggcggcc acaccctggc gtgcaccgag ccggagcccg gataagcacg gtaaggagag
1261 tacggcggga cgtggcgacc cgtgtgtctg ctgccacgca gccttcctcc acgtagccgc
1321 gcggccgcgc cacgtaccag ggcccggcgc tggtataaat gcgcgccacc tccgctttag
1381 ttctgcatac agccaaccca a
```

GGATCCAACACACACCCGAGGATATCACAGTCGACACTACACC

Figure 2 cggtatgaatttggaaacaaattcagtactttaaaaaaatttgttgtagggagcaaataatacataaaataatttatgcattattttattt
tttatttgtaataatatgcttgaaacgataattcagtatgcatgttgtgccagtgtactacacgggcgggggggaggggattgagtgg
gccagcgcggtgcgtagggtagatgggctgaaattgataactcaagtccgactaggttctcttttatttcccttcctttctattttcct
ttcttttaattttcatgctttcaaactaaattcaaattcgagttttgaatttcagcttctaaattgtacactaaaattatatgataaggtaacc
cctactattactttaatttttttattctaccccatattgtttacttaggggagaataattgacttaatcacattcttcctaggtttcaattctca
atctttcaaatccacattttagatttctattttgaatttaaataccagtttggatttagagttcaatttcaaaatacacaaccaaaatacca
gcatgaatgcaaatatattttatgtttatgtatttactttctttttatactttgctcaaaatagttattttcatgtatgaaactcaataagcaag
gaactcacgttattatataacctaataggaataatttaggtaacataatttatcatcctcttgatttaaaagagatatgcctccagaata
agacacatactaaaaataactctaatattgaataactaaagtcgtacaaatctctactattattcctataaaataataaagaactagcta
caacttctttaaggcattattcagggtttacagcttgagaggcatgaacccatcctgtatactcctggacttggaagacaaaatgtca
accaaagtgaaaggttttcttatggttgctgctaagagatagattgaacactagatctctcctaagacgtcagggcatgcgtttaga
ctcctacacatgcgaaaactgcatcttacagttggaagaaactatatctcaccacttcctgcggtgtaactttgcccaaagatgttgg
ctcactgttggaatcactccgccccgaactttggatctaacgcttgcagtgctacatattagagcaagactaacaatgccgtggag
aatggaaggtattataaccatgtcatggtgcatatggaaatgtcgaaataactggatattcgaaaacataccgccaacggtggcg
gcctgcaaggaaatgttcaagactgaaatgaactacatctgctaccaagttaagctcgagacaggagctaaaagtagaaactgg
atacaacactttgtaacatagtgacactccccttttcctttctttaccttagaactatacatacaatccacattcaataaaaatttgtagg
tacgccatacacactaccggaatccggctctttgccgagtgtgaggcgctttgtcgagtgctttttgtccagcactcggcaaaaaa
gtctttgccatgtgccgcactcggcaaagtcctgctctcggtaacgaccgcgtttaccgagagcaggactctcgacacagaaata
cactcgacaaagaaatctttgccgagagccaaacactcggcgaacggcagcgctcggcaaagggtcgtcagccgccgtctaa
agctgacggtcgttatctttgtcgagtgccccctcgtccgacactcagtagagcaagcttgccgagtgccatccttggacactcga
taaagtatattttatttttttttatttgccaaccaaacttttgtggtatgttcctacactatgtagatctacatgtaccatttggcacaatta
caaaaatgtttctataactattagatttagttcgtttatttgaatttcttcggaaaattcacatatgaactgcaagtcactcgaaacatga
aaaaccgtgcatgcaaaataaatgatatgcatgttatctagcacaagttacgaccgaattcagaagcagaccagaatcttcaagc
accatgctcactaaacatgaccgtgaacttgttatccagttgtttaaaaattgtataaaacacaaataaagtcagaaattaatgaaact
tgtccacatgtcatgatatcatatatagaggttgtgataaaaatttgataatgtttcggtaaagttgtgacgtactatgtgtagaaacct
aagtgacctacacataaaatcatagagtttcaatgtagttcactcgacaaagactttgtcaagtgtccgataaaaagtattcagcaa
agaagccgttgtcgatttactgttcgtcgagatctctttgccgagtgtcacactaggcaaagtctttacggagtgtttttcaggctttg
acactcggcaaagcgctcgattccagtagtgacagtaatttgcatcaaaaatagccgagagatttaaaatgagtcaactaatagac
caactaattattagctattagtcgttagcttctttaatctaagctaaaaccaactaatagcttatttgttgaattacaattagctcaacgga
attctctgtttttctataaaaaaaagggaaactgcccctcatttacagcaaactgtccgctgcctgtcgtccagatacaatgaacgta
cctagtaggaactctttacacgctcggtcgctcgccgcggatcggagtcccaggaacacgacaccactgtggaacacgacaa
agtctgctcagaggcggccacaccctggcgtgcaccgagccggagcccggataagcacggtaaggagagtacggcgggac
gtggcgacccgtgtgtctgctgccacgcagccttcctccacgtagccgcgcggccgcgccacgtaccagggcccggcgctgg
tataaatgcgcgccacctccgctttagttctgcatacagccaacccaacacacacccgagcatatcacagtgacagacacta
cacgATG

Figure 3

AscI

~~~~~~~~

| | | | | | |
|---|---|---|---|---|---|
| 1 | GGCGCGCCGG | TATGAATTTG | GAAACAAATT | CAGTACTTTT | AAAAAAATTT |
| 51 | GTTGTAGGGA | GCAAATAATA | CATAAAATAA | TTTATGCATT | ATTTTATTTT |
| 101 | TTATTTGTAA | TAATATGCTT | GAAACGATAA | TTCAGTATGC | ATGTTGTGCC |
| 151 | AGTGTACTAC | ACGGGCGGGG | GGAGGCGATT | GAGTGGGCCA | GCGCGGTGCG |
| 201 | TAGGGTAGAT | GGGCTGAAAT | TGATAACTCA | AGTCCGACTA | GGTTCTCTTT |
| 251 | TTATTTCCCT | TCCTTTTCTA | TTTTCCTTTC | TTTTAATTTT | CATGCTTTCA |
| 301 | AACTAAATTC | AAATTCGAGT | TTTGAATTTC | AGCTTCTAAA | TTGTACACTA |
| 351 | AAATTATATG | ATAAGGTAAC | CCCTACTATT | ACTTTTAATT | TTTTTATTCT |
| 401 | ACCCCATATT | GTTTACTTAG | GGGAGAATAA | TTGACTTAAT | CACATTCTTC |
| 451 | CTAGGTTTCA | ATTCTCAATC | TTTCAAATCC | ACATTTTTAG | ATTTCTATTT |
| 501 | TGAATTTAAA | TACCAGTTTG | GATTTAGAGT | TCAATTTCAA | AATACACAAC |
| 551 | CAAAATACCA | GCATGAATGC | AAATATATTT | TATGTTTATG | TATTTACTTT |
| 601 | TCTTTTATAC | TTTGCTCAAA | ATAGTTATTT | TCATGTATGA | AACTCAATAA |
| 651 | GCAAGGAACT | CACGTTATTA | TATAACCTAA | TAGGAATAAT | TTAGGTAACA |
| 701 | TAATTTATCA | TCCTCTTGAT | TTAAAAGAGA | TATGCCTCCA | GAATAAGACA |
| 751 | CATACTAAAA | ATAACTCTAA | TATTGAATAA | CTAAAGTCGT | ACAAATCTCT |
| 801 | ACTATTATTC | CTATAAAATA | ATAAAGAACT | AGCTACAACT | TCTTTAAGGC |
| 851 | ATTATTCAGG | GTTTACAGCT | TGAGAGGCAT | GAACCCATCC | TGTATACTCC |
| 901 | TGGACTTGGA | AGACAAAATG | TCAACCAAAG | TGAAAGGTTT | TCTTATGGTT |
| 951 | GCTGCTAAGA | GATAGATTGA | ACACTAGATC | TCTCCTAAGA | CGTCAGGGCA |
| 1001 | TGCGTTTAGA | CTCCTACACA | TGCGAAAACT | GCATCTTACA | GTTGGAAGAA |
| 1051 | ACTATATCTC | ACCACTTCCT | GCGGTGTAAC | TTTGCCCAAA | GATGTTGGCT |
| 1101 | CACTGTTGGA | ATCACTCCGC | CCCGAACTTT | GGATCTAACG | CTTGCAGTGC |
| 1151 | TACATATTAG | AGCAAGACTA | ACAATGCCGT | GGAGAATGGA | AGGTATTATA |
| 1201 | ACCATGTCAT | GGTGCATATG | GAAATGTCGA | AATAACTGGA | TATTCGAAAA |
| 1251 | CATACCGCCA | ACGGTGGCGG | CCTGCAAGGA | AATGTTCAAG | ACTGAAATGA |
| 1301 | ACTACATCTG | CTACCAAGTT | AAGCTCGAGA | CAGGAGCTAA | AAGTAGAAAC |
| 1351 | TGGATACAAC | ACTTTGTAAC | ATAGTGACAC | TCCCCTTTTC | CTTTCTTTTA |
| 1401 | CCTTAGAACT | ATACATACAA | TCCACATTCA | ATAAAAATTT | GTAGGTACGC |
| 1451 | CATACACACT | ACCGGAATCC | GGCTCTTTGC | CGAGTGTGAG | GCGCTTTGTC |
| 1501 | GAGTGCTTTT | TGTCCAGCAC | TCGGCAAAAA | AGTCTTTGCC | ATGTGCCGCA |
| 1551 | CTCGGCAAAG | TCCTGCTCTC | GGTAACGACC | GCGTTTACCG | AGAGCAGGAC |
| 1601 | TCTCGACACA | GAAATACACT | CGACAAAGAA | ATCTTTGCCG | AGAGCCAAAC |
| 1651 | ACTCGGCGAA | CGGCAGCGCT | CGGCAAAGGG | TCGTCAGCCG | CCGTCTAAAG |
| 1701 | CTGACGGTCG | TTATCTTTGT | CGAGTGCCCC | CTCGTCCGAC | ACTCAGTAGA |
| 1751 | GC*ACGCGCC*G | GTATGAATTT | GGAAACAAAT | TCAGTACTTT | TAAAAAAATT |
| 1801 | TGTTGTAGGG | AGCAAATAAT | ACATAAAATA | ATTTATGCAT | TATTTTATTT |
| 1851 | TTTATTTGTA | ATAATATGCT | TGAAACGATA | ATTCAGTATG | CATGTTGTGC |
| 1901 | CAGTGTACTA | CACGGGCGGG | GGGAGGGGAT | TGAGTGGGCC | AGCGCGGTGC |
| 1951 | GTAGGGTAGA | TGGGCTGAAA | TTGATAACTC | AAGTCCGACT | AGGTTCTCTT |
| 2001 | TTTATTTCCC | TTCCTTTTCT | ATTTTCCTTT | CTTTTAATTT | TCATGCTTTC |
| 2051 | AAACTAAATT | CAAATTCGAG | TTTTGAATTT | CAGCTTCTAA | ATTGTACACT |
| 2101 | AAAATTATAT | GATAAGGTAA | CCCCTACTAT | TACTTTTAAT | TTTTTTATTC |
| 2151 | TACCCCATAT | TGTTTACTTA | GGGGAGAATA | ATTGACTTAA | TCACATTCTT |
| 2201 | CCTAGGTTTC | AATTCTCAAT | CTTTCAAATC | CACATTTTTA | GATTTCTATT |
| 2251 | TTGAATTTAA | ATACCAGTTT | GGATTTAGAG | TTCAATTTCA | AAATACACAA |
| 2301 | CCAAAATACC | AGCATGAATG | CAAATATATT | TTATGTTTAT | GTATTTACTT |
| 2351 | TTCTTTTATA | CTTTGCTCAA | AATAGTTATT | TTCATGTATG | AAACTCAATA |
| 2401 | AGCAAGGAAC | TCACGTTATT | ATATAACCTA | ATAGGAATAA | TTTAGGTAAC |
| 2451 | ATAATTTATC | ATCCTCTTGA | TTTAAAAGAG | ATATGCCTCC | AGAATAAGAC |
| 2501 | ACATACTAAA | AATAACTCTA | ATATTGAATA | ACTAAAGTCG | TACAAATCTC |
| 2551 | TACTATTATT | CCTATAAAAT | AATAAAGAAC | TAGCTACAAC | TTCTTTAAGG |
| 2601 | CATTATTCAG | GGTTTACAGC | TTGAGAGGCA | TGAACCCATC | CTGTATACTC |
| 2651 | CTGGACTTGG | AAGACAAAAT | GTCAACCAAA | GTGAAAGGTT | TTCTTATGGT |
| 2701 | TGCTGCTAAG | AGATAGATTG | AACACTAGAT | CTCTCCTAAG | ACGTCAGGGC |
| 2751 | ATGCGTTTAG | ACTCCTACAC | ATGCGAAAAC | TGCATCTTAC | AGTTGGAAGA |

Figure 4A
~~~~~~~~

2801 AACTATATCT CACCACTTCC TGCGGTGTAA CTTTGCCCAA AGATGTTGGC
2851 TCACTGTTGG AATCACTCCG CCCCGAACTT TGGATCTAAC GCTTGCAGTG
2901 CTACATATTA GAGCAAGACT AACAATGCCG TGGAGAATGG AAGGTATTAT
2951 AACCATGTCA TGGTGCATAT GGAAATGTCG AAATAACTGG ATATTCGAAA
3001 ACATACCGCC AACGGTGGCG GCCTGCAAGG AAATGTTCAA GACTGAAATG
3051 AACTACATCT GCTACCAAGT TAAGCTCGAG ACAGGAGCTA AAAGTAGAAA
3101 CTGGATACAA CACTTTGTAA CATAGTGACA CTCCCCTTTT CCTTTCTTTT
3151 ACCTTAGAAC TATACATACA ATCCACATTC AATAAAAATT TGTAGGTACG
3201 CCATACACAC TACCGGAATC CGGCTCTTTG CCGAGTGTGA GGCGCTTTGT
3251 CGAGTGCTTT TTGTCCAGCA CTCGGCAAAA AAGTCTTTGC CATGTGCCGC
3301 ACTCGGCAAA GTCCTGCTCT CGGTAACGAC CGCGTTTACC GAGAGCAGGA
3351 CTCTCGACAC AGAAATACAC TCGACAAAGA AATCTTTGCC GAGAGCCAAA
3401 CACTCGGCGA ACGGCAGCGC TCGGCAAAGG GTCGTCAGCC GCCGTCTAAA
3451 GCTGACGGTC GTTATCTTTG TCGAGTGCCC CCTCGTCCGA CACTCAGTAG
3501 AGC*ACGCGCC* GGTATGAATT TGGAAACAAA TTCAGTACTT TTAAAAAAAT
3551 TTGTTGTAGG GAGCAAATAA TACATAAAAT AATTTATGCA TTATTTTATT
3601 TTTTATTTGT AATAATATGC TTGAAACGAT AATTCAGTAT GCATGTTGTG
3651 CCAGTGTACT ACACGGGCGG GGGGAGGGGA TTGAGTGGGC CAGCGCGGTG
3701 CGTAGGGTAG ATGGGCTGAA ATTGATAACT CAAGTCCGAC TAGGTTCTCT
3751 TTTTATTTCC CTTCCTTTTC TATTTTCCTT TCTTTTAATT TTCATGCTTT
3801 CAAACTAAAT TCAAATTCGA GTTTTGAATT TCAGCTTCTA AATTGTACAC
3851 TAAAATTATA TGATAAGGTA ACCCCTACTA TTACTTTTAA TTTTTTTATT
3901 CTACCCCATA TTGTTTACTT AGGGGAGAAT AATTGACTTA ATCACATTCT
3951 TCCTAGGTTT CAATTCTCAA TCTTTCAAAT CCACATTTTT AGATTTCTAT
4001 TTTGAATTTA AATACCAGTT TGGATTTAGA GTTCAATTTC AAAATACACA
4051 ACCAAAATAC CAGCATGAAT GCAAATATAT TTTATGTTTA TGTATTTACT
4101 TTTCTTTTAT ACTTTGCTCA AAATAGTTAT TTTCATGTAT GAAACTCAAT
4151 AAGCAAGGAA CT*CACGTT*AT TATATAACCT AATAGGAATA ATTTAGGTAA
4201 CATAATTTAT CATCCTCTTG ATTTAAAAGA GATATGCCTC CAGAATAAGA
4251 CACATACTAA AAATAACTCT AATATTGAAT AACTAAAGTC GTACAAATCT
4301 CTACTATTAT TCCTATAAAA TAATAAAGAA CTAGCTACAA CTTCTTTAAG
4351 GCATTATTCA GGGTTTACAG CTTGAGAGGC ATGAACCCAT CCTGTATACT
4401 CCTGGACTTG GAAGACAAAA TGTCAACCAA AGTGAAAGGT TTTCTTATGG
4451 TTGCTGCTAA GAGATAGATT GAACACTAGA TCTCTCCTAA *GACGTC*AGGG
4501 CATGCGTTTA GACTCCTACA CATGCGAAAA CTGCATCTTA CAGTTGGAAG
4551 AAACTATATC TCACCACTTC CTGCGGTGTA ACTTTGCCCA AAGATGTTGG
4601 CTCACTGTTG GAATCACTCC GCCCCGAACT TTGGATCTAA CGCTTGCAGT
4651 GCTACATATT AGAGCAAGAC TAACAATGCC GTGGAGAATG GAAGGTATTA
4701 TAACCATGTC ATGGTGCATA TGGAAATGTC GAAATAACTG GATATTCGAA
4751 AACATACCGC CAACGGTGGC GGCCTGCAAG GAAATGTTCA AGACTGAAAT
4801 GAACTACATC TGCTACCAAG TTAAGCTCGA GACAGGAGCT AAAAGTAGAA
4851 ACTGGATACA ACACTTTGTA ACATAGTGAC ACTCCCCTTT TCCTTTCTTT
4901 TACCTTAGAA CTATACATAC AATCCACATT CAATAAAAAT TTGTAGGTAC
4951 GCCATACACA CTACCGGAAT CCGGCTCTTT GCCGAGTGTG AGGCGCTTTG
5001 TCGAGTGCTT TTTGTCCAGC ACTCGGCAAA AAAGTCTTTG CCATGTGCCG
5051 CACTCGGCAA AGTCCTGCTC TCGGTAACGA CCGCGTTTAC CGAGAGCAGG
5101 ACTCTCGACA CAGAAATACA CTCGACAAAG AAATCTTTGC CGAGAGCCAA
5151 ACACTCGGCG AACGGCAGCG CTCGGCAAAG GGTCGTCAGC CGCCGTCTAA
5201 AGCTGACGGT CGTTATCTTT GTCGAGTGCC CCCTCGTCCG ACACTCAGTA
HindIII
~~~~~~~~
5251 GAGCAAGCTT GCCGAGTGCC ATCCTTGGAC ACTCGATAAA GTATATTTTA
5301 TTTTTTTTTA TTTTGCCAAC CAAACTTTTT GTGGTATGTT CCTACACTAT
5351 GTAGATCTAC ATGTACCATT TTGGCACAAT TACAAAAATG TTTTCTATAA
5401 CTATTAGATT TAGTTCGTTT ATTTGAATTT CTTCGGAAAA TTCACATATG
5451 AACTGCAAGT CACTCGAAAC ATGAAAAACC GTGCATGCAA AATAAATGAT
5501 ATGCATGTTA TCTAGCACAA GTTACGACCG AATTCAGAAG CAGACCAGAA
5551 TCTTCAAGCA CCATGCTCAC TAAACATGAC CGTGAACTTG TTATCCAGTT
5601 GTTTAAAAAT TGTATAAAAC ACAAATAAAG TCAGAAATTA ATGAAACTTG Figure 4B
~~~~~~~~

5651 TCCACATGTC ATGATATCAT ATATAGAGGT TGTGATAAAA ATTTGATAAT
5701 GTTTCGGTAA AGTTGTGACG TACTATGTGT AGAAACCTAA GTGACCTACA
5751 CATAAAATCA TAGAGTTTCA ATGTAGTTCA CTCGACAAAG ACTTTGTCAA
5801 GTGTCCGATA AAAAGTATTC AGCAAAGAAG CCGTTGTCGA TTTACTGTTC
5851 GTCGAGATCT CTTTGCCGAG TGTCACACTA GGCAAAGTCT TTACGGAGTG
5901 TTTTTCAGGC TTTGACACTC GGCAAAGCGC TCGATTCCAG TAGTGACAGT
5951 AATTTGCATC AAAAATAGCC GAGAGATTTA AAATGAGTCA ACTAATAGAC
6001 CAACTAATTA TTAGCTATTA GTCGTTAGCT TCTTTAATCT AAGCTAAAAC
6051 CAACTAATAG CTTATTTGTT GAATTACAAT TAGCTCAACG GAATTCTCTG
6101 TTTTTTCTAT AAAAAAAAGG GAAACTGCCC CTCATTTACA GCAAACTGTC
6151 CGCTGCCTGT CGTCCAGATA CAATGAACGT ACCTAGTAGG AACTCTTTTA
6201 CACGCTCGGT CGCTCGCCGC GGATCGGAGT CCCAGGAACA CGACACCACT
6251 GTGGAACACG ACAAAGTCTG CTCAGAGGCG GCCACACCCT GGCGTGCACC
6301 GAGCCGGAGC CCGGATAAGC ACGGTAAGGA GAGTACGGCG GGACGTGGCG
6351 ACCCGTGTGT CTGCTGCCAC GCAGCCTTCC TCCACGTAGC CGCGCGGCCG
6401 CGCCACGTAC CAGGGCCCGG CGCTGG*TATA AAT*GCGCGCC ACCTCCGCTT
6451 TAGTTCTGCA TACAGCCAAC CCAACACACA CCCGAGCATA TCACAGTGAC
NcoI
~~~~~~
6501 AGACACTACA CCatgGCCAA CAAGCACCTG AGCCTCTCCC TCTTCCTCGT
6551 GCTCCTCGGC CTCTCCGCCT CCCTCGCCAG CGGC*GAGTCC ACCACCTCCG*
*6601 GCTTCCTCGG CCCGCTCCTC GTGCTCCAGG CCGGCTTCTC CCTCCTCACC*
*6651 CGCATCCTCA CCATCCCGCA GTCCCTCGAC TCCTGGTGGA CCTCCCTCAA*
*6701 CTTCCTCGGC GGCGCCCCGA CCTGCCCGGG CCAGAACCTC CAGTCCCCGA*
*6751 CCTCCAACCA CTCCCCGACC TCCTGCCCGC CCACCTGCCC GGGCTACCGC*
*6801 TGGATGTGCC TCCGCCGCTT CATCATCTTC CTCTTCATCC TCCTGCTCTG*
*6851 CCTCATCTTC CTCCTCGTGC TCGTGGACTA CCAGGGCATG CTCCCGGTGT*
*6901 GCCCGCTCCT CCCGGGCACC TCCACGACCT CCACCGGCCC GTGCAAGACC*
*6951 TGCACCATCC CGGCCCAGGG CACCTCCATG TTCCCGTCCT GCTGCTGCAC*
*7001 CAAGCCGTCC GACGGCAACT GCGCCTGCAT CCCGATCCCG TCCTCCTGGG*
*7051 CCTTCGCCCG CTTCCTCTGG GAGTGGGCCT CCGTGCGCTT CTCCTGGCTC*
*7101 TCCCTCCTCG TGCCGTTCGT GCAGTGGTTC GTGGGCCTCT CCCCGACCGT*
*7151 GTGGCTCTCC GTGATCTGGA TGATGTGGTA CTGGGGCCCG TCCCTCTACA*
*7201 ACATCCTCTC CCCGTTCCTC CCGCTCCTCC CGATCTTCTT CTGCCTCTGG*
*7251 GTGTACATCCt ga*

Figure 4C

REGULATORY REGION HAVING INCREASED EXPRESSION AND METHOD OF USING SAME

REFERENCE TO RELATED APPLICATION

This application claims priority to previously filed and co-pending application U.S. Ser. No. 61/512,347, filed Jul. 27, 2011, the contents of which are incorporated herein by reference in its entirety.

This invention was made with government support under Grant Number 1 R43 AI068239-01A1 awarded by the National Institute of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Jul. 26, 2012, is named AB00014.txt and is 48,174 bytes in size.

BACKGROUND OF THE INVENTION

Promoters are vital molecular tools that have been applied widely in plant biotechnology to control the expression of introduced genes. There are many applications for promoters in driving gene expression in plant tissues. These include the synthesis of scoreable and selectable markers to identify transgenic plants (Jefferson et al., 1987; Wohlleben et al., 1988) and the over-expression of control point enzymes to modify metabolic flux through key pathways, so affecting the yields of important plant products (Nessler, 1994; Lessard et al., 2002). Other uses of plant promoters include the expression of genes conferring resistance to pests, thus conferring protection (Estruch et al., 1997), and the expression of non-native enzymes to facilitate the production of foreign metabolites in particular plant species (Poirier et al., 1995; Ye et al., 2000). A further application of plant promoters is to over-express controlling regulatory genes affecting aspects of plant physiology such as flowering time and so modify plant growth characteristics (Weigel and Nilsson, 1995). Promoters are also used to repress the expression of specific genes by driving the synthesis of interfering RNA species (Waterhouse et al., 2001), thus affecting plant metabolic and developmental pathways (Yu and Kumar, 2003). Although high levels of expression may not be necessary for all of the above applications, there is clearly a need for promoters showing activity in plant tissues.

Apart from these and other applications of promoters to modify plant traits, promoters are also required for plants to act as production systems for heterologous proteins. Plants have been used to produce a wide range of recombinant proteins of potential economic and/or medicinal importance. These include research chemicals (Hood et al., 1997; Zhong et al., 1999), processing enzymes that are used, for example, in the pharmaceutical industry (Woodard et al., 2003), industrial enzymes that are deployed in large-scale processing operations such as bleaching (Hood et al., 2003; Bailey et al., 2004), candidate vaccine antigens for animal or plant disease prevention (Mason et al., 1992; Haq et al., 1995; Carrillo et al., 1998; Streatfield et al., 2001), and therapeutic pharmaceuticals including antibodies (Daniell et al., 2001; Hood et al., 2002). The expressed proteins may either be purified from the plant tissues (Hood et al., 1997; Woodard et al., 2003) or, if as with vaccines the final application allows it, the recombinant plant material may be processed into a suitable form for use or even deployed directly (Streatfield et al., 2002; Lamphear et al., 2002). For these and other protein products to be produced in plant systems it is necessary that promoters drive a sufficiently high level of expression to ensure commercial viability.

Spatial and temporal control is also often important in driving gene expression in plants. For example selectable and scoreable markers must be expressed at a suitable time and in an appropriate tissue to allow for screening, and controlling enzymes and regulatory factors must be produced in metabolically active and physiologically responsive tissues, respectively. Similarly, genes conferring host protection must be expressed in the target tissues for the pathogen or pest, and plant produced protein products should be expressed in tissues suitable for protein accumulation and storage. Furthermore, since certain protein products may have detrimental effects on plant health and yield when expressed in metabolically active plant tissues that are essential for survival and growth, promoters may be favored that are active in the chosen plant storage tissues but show low or no activity in other, non-storage tissues.

Promoters that preferentially express relatively high levels of foreign proteins in tissues suitable for stable protein accumulation and storage are particularly useful for commercial protein production. The seed tissues of the cereals are especially well suited to the large-scale production of recombinant proteins. Thus, there is a requirement for promoters that show a seed tissue preferred expression pattern in plants and particularly cereals and drive relatively high levels of protein accumulation in these tissues.

Several promoters of plant and plant pathogen (bacterial and viral) origin have been used to direct transgene expression in plants. Prominent examples include the French bean beta-phaseolin promoter (Bustos et al., 1989), the mannopine synthase promoter of *Agrobacterium tumefaciens* (Leung et al., 1991), and the 35S promoter of cauliflower mosaic virus (Guilley et al., 1982). These and several other promoters in widespread use in plants were originally developed and utilized in dicot species. Promoter sequences from one species are predictably used in other species (see discussion below). The cereals comprise particularly important crops and there is therefore a pressing need for promoters that have high activity and/or tissue preference in monocots. Cereals, such as grasses, are cultivated for their grain. Since the nutritional value of cereals is in their seeds, and these tissues are also well suited for recombinant protein accumulation and storage, promoters that are active in cereal seed tissues are especially useful.

Two broad classes of promoters are typically deployed: constitutive and tissue preferred. Constitutive promoters, such as maize polyubiquitin-1 drive expression in the seed but also in other tissues (Christensen et al., 1992). A drawback with such constitutive promoters is that expression in tissues other than seed storage tissues may result in plant health being compromised, for example if a potentially toxic protein is expressed in metabolically active tissues required for germination or growth (Hood et al., 2003). Furthermore, constitutive expression may result in the expressed foreign protein being synthesized in pollen grains and thus being difficult to contain. By contrast, seed preferred promoters limit all or the bulk of transgene expression to seed tissues, so avoiding such concerns. Tissue preferred expression can include seed preferred expression. An example of one such promoter providing seed preferred expression is the phaseolin promoter. See, Bustos et al.

"Regulation of β-glucuronidase Expression in Transgenic Tobacco Plants by an A/T-Rich cis-Acting Sequence Found Upstream of a French Bean β-Phaseolin Gene" *The Plant Cell* Vol. 1, 839-853 (1989).

There is a need for further promoters that express transgenes at increased levels to those currently used. Such promoters are especially useful with tissue-preferred promoters.

All references cited herein are incorporated herein by reference.

SUMMARY OF THE INVENTION

A globulin-1 regulatory region has preferential expression to the embryo of a plant. This invention increases expression by providing for an enhanced globulin-1 regulatory region, which provides for a globulin-1 regulatory region and upstream at least one copy and in another embodiment at least two copies of the globulin-1 regulatory region or fragments thereof. The additional copies of the globulin-1 regulatory region or fragments will comprise at least one of the transcriptional binding domains of the globulin-1 regulatory region. The enhanced globulin-1 regulatory region will also comprise a transcription initiation site that includes a translation start site. In one embodiment the promoter comprises a sequence having at least one copy of SEQ ID NO: 10 upstream of a globulin-1 promoter. Another embodiment provides that the enhanced globulin-1 regulatory region comprises SEQ ID NO: 12 and at least one copy of SEQ ID NO: 10. An embodiment further provides for the globulin-1 regulatory region or fragments thereof to comprise SEQ ID NO: 3, 4, 6 or 7. One embodiment provides the binding region is selected from SEQ ID NO: 16-30. In a further embodiment, such a promoter is used to drive expression preferentially to embryos in plants.

DESCRIPTION OF THE DRAWINGS

FIG. 1A shows the nucleotide sequence (SEQ ID NO: 1) and FIG. 1B shows the encoded amino acid sequence (SEQ ID NO: 2) of the β-glucuronidase gene used in experiments.

FIG. 2 shows the nucleotide sequence of the Belanger et al. 1401 bp globulin-1 regulatory region nucleotide sequence (SEQ ID NO: 3). The promoter is bases 1-1386 (SEQ ID NO: 4), the TATA box is at 1354-1360 and the 5'UTR is 1387-1401 (shown in italics, SEQ ID NO: 5). Below the sequence is an additional 43 bases (SEQ ID NO: 31) of maize chromosome 1 included with the sequence in certain constructs described in the experiments.

FIG. 3 shows the nucleotide sequence of the proximal approximately 3 kb of DNA upstream of the extended globulin-1 translation start codon. The untranslated leader sequence is given in bold type and the translation start codon is capitalized. The entire sequence is SEQ ID NO: 6, the promoter is SEQ ID NO: 7 and the untranslated leader sequence is SEQ ID NO: 8.

FIG. 4 A-C shows the sequences of an enhanced globulin-1 regulatory region and associated coding sequences used in the experiments, including restriction sites and sequences annotated as described below (SEQ ID NO: 9).

BRIEF DESCRIPTION OF THE SEQUENCES

Figure 5:
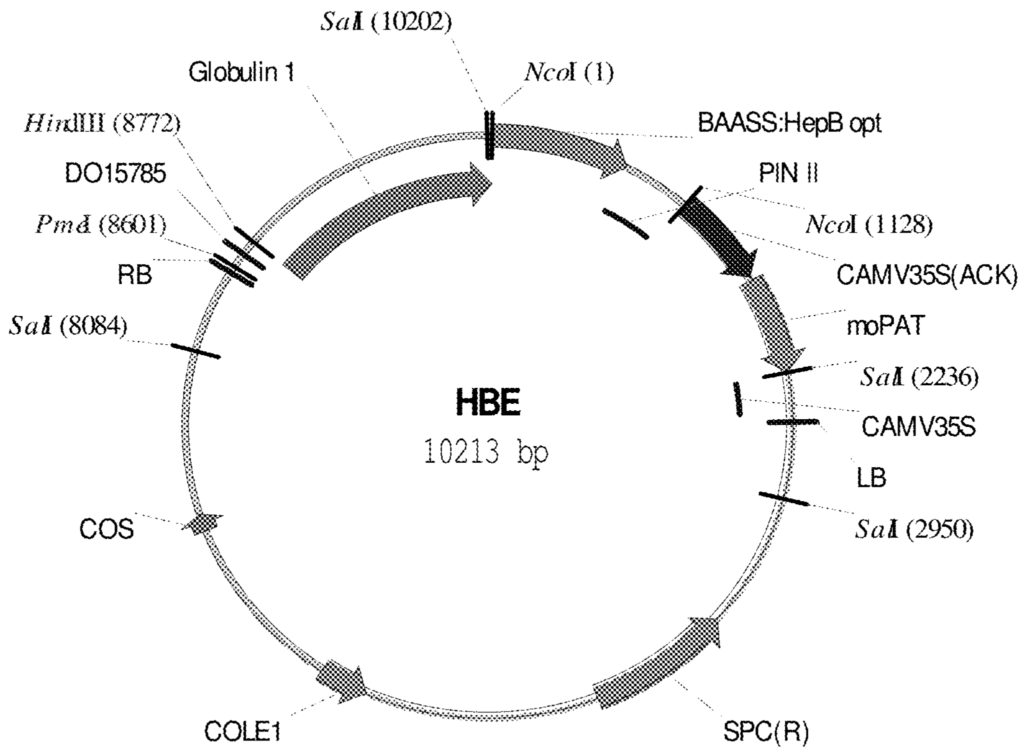
FIG. 5 is a map of plasmid HBE used in the experiments below.

SEQ ID NO: 1: β-glucuronidase nucleotide sequence

SEQ ID NO: 2: β-glucuronidase amino acid sequence

SEQ ID NO: 3: globulin-1 regulatory region nucleotide sequence

SEQ ID NO: 4: globulin-1 promoter

SEQ ID NO: 5: globulin-1 5' UTR

SEQ ID NO: 6: extended globulin-1 regulatory region nucleotide sequence

SEQ ID NO: 7: extended globulin-1 promoter

SEQ ID NO: 8: extended globulin-1 leader sequence

SEQ ID NO: 9: enhanced globulin-1 sequences with restriction sites, hepatitis B coding sequence and BAASS sequences SEQ ID NO: 10: The first, second and third repeat of enhanced globulin-1 regulatory region which repeat is the first 1745 bases of SEQ ID NO: 6.

SEQ ID NO: 11: the extended globulin-1 regulatory region including leader sequence used in the experiments below, which is the same as the extended globulin-1 regulatory region of the '967 patent, except that base 6512 is C instead of G SEQ ID NO: 12: non-repeat region of globulin-1 promoter, which is bases 5255-6459 of SEQ ID NO: 9

SEQ ID NO: 13: leader sequence including transcription initiation site of enhanced globulin-1

SEQ ID NO: 14: Barley alpha amylase signal sequence

SEQ ID NO: 15: hepatitis B sequence of GENBANK® (known as GenBank in citations, is a sequence database incorporating publicly available DNA sequences), accession S62754.

SEQ ID NO: 16: Ry-repeat/SphI element consensus sequence

SEQ ID NO: 17: Sph element 1

SEQ ID NO: 18: Sph element 2

SEQ ID NO: 19: Sph element 3

SEQ ID NO: 20: Sph element 4

SEQ ID NO: 21: Sph element 5

SEQ ID NO: 22: Sph element 6

SEQ ID NO: 23: Sph element 7

SEQ ID NO: 24: Sph element 8

SEQ ID NO: 25: Sph element 9:

SEQ ID NO: 26: Sph element 10

SEQ ID NO: 27: ABRE consensus element rice

SEQ ID NO: 28: ABRE consensus element *Arabidopsis*

SEQ ID NO: 29: ABRE element 1

SEQ ID NO: 30: ABRE element 2

SEQ ID NO: 31: region of maize chromosome 1

Description of the Preferred Embodiments

Nucleotide sequences are described herein that regulate transcription with preferential expression to plant seed tissue, and preferential expression to plant embryo tissue in the seed. The invention is to an enhanced globulin-1 promoter having increased expression.

Globulin-1 is the most abundant protein in maize embryos and is a vicilin-like storage protein encoded by the globulin-1 gene. See, e.g., Liu et al. (1992) *MNL* Vol. 22: 108-109. As noted in Belanger et al. (1991) globulins are storage proteins recognized as comprising 10-20% of the maize embryo protein and Globulin 1 is one of the most abundant proteins, encoded by the globulin-1 gene. Belanger, F. C. and Kriz, A. L. (1991) "Molecular basis for allelic polymorphism of the maize globulin-1 gene" *Genetics* 129, 863-872. The two most abundant proteins in maize embryos are saline-soluble, water-insoluble globulins, one being a 63,000 Da molecular weight protein encoded by the globulin-1 gene, the other a 45,000 Da molecular weight protein encoded by the globulin-2 gene. See. E.g, Kriz (1989) *Biochem Genet.* 27(3-4):238-51. Where a null allele is present no Globulin 1 protein is produced. Belanger et al. (1991), supra. Belanger et al. note that the protein is readily detected in a Coomassie-stained gel of protein extracts from embryos and several alleles have been recognized. Belanger et al. (1991), at 865. One skilled in the art appreciates that nucleic acid molecules that encode the Globulin 1 protein are well known and readily identified using techniques available to one skilled in the art and as discussed here, including, by way of example without limitation, comparison to known sequences, preparation of a library and screening with a probe, antibody binding, using Northern, Southern or Western blots, among the many avenues available. To recapitulate, when referring to a globulin-1 promoter is meant the regulatory element of a nucleic acid molecule which encodes Globulin 1. The promoter of a globulin-1 encoding gene may be used in plants to express operably linked nucleic acid molecules in a plant. Examples, without intending to be limiting, of globulin promoters include the 1.45 kb maize globulin-1 promoter plus untranslated leader described by Belanger and Kriz, 1991, supra and). GenBank® accession L22344 (SEQ ID NO: 3 and shown in FIG. 2 Another example of a globulin-1 promoter which may be employed in the invention are nucleotide sequences natively associated with the nucleotide sequence coding for *Zea mays* extended globulin-1 and comprise SEQ ID NO: 6 and is shown in FIG. 3. This promoter was first described in U.S. Pat. No. 7,169,967, incorporated herein by reference in its entirety.

The extended globulin-1 regulatory sequence is shown in FIG. 3. This is SEQ ID NO: 6 and includes the proximal approximately 3 kb of a maize extended globulin-1 promoter plus untranslated leader. Transgenic plants generated using this sequence show significantly increased expression over those generated using a previously cloned approximately 1.45 kb maize globulin-1 promoter plus untranslated leader (SEQ ID NO: 3), which has previously been deployed to express transgenes in maize seeds (Hood et al., 2003; Woodard et al., 2003). The extended globulin-1 promoter plus untranslated leader sequence of patent '967 is highly embryo preferred in its expression pattern, as is the previously cloned globulin-1 promoter sequence of Belanger et al.

The inventors have here discovered that where a globulin-1 promoter region comprising at least one transcriptional binding domain is repeated at least two times in a DNA construct, expression of an operably linked nucleic acid is increased over the expression obtained when a single copy of the promoter is used to drive expression of the linked nucleic acid. Further, it shows improved expression compared to use of two constructs using the promoter operably linked to a nucleic acid.

In an embodiment the promoter has at the 5' end an additional at least one copy of the region which comprises the promoter or a fragment comprising at least one transcriptional binding domain, thereby providing at least two repeats of this region. An embodiment provides the 3' end of the promoter is unchanged. In the construct will also be included the transcription start site including the translation site ATG. As one skilled in the art will appreciate, the initiation start site and translation start site is provided as one copy. Together, the globulin-1 promoter or fragment comprising at least one binding domain, repeated two or three times, and the transcription/translation start site are referred to herein as the enhanced globulin-1 promoter. In an embodiment, the one or two copies are upstream of a globulin-1 promoter. The exact sequence will vary, as one skilled in the art will appreciate, as long as at least one binding site is included in at least one copy. By way of example, the construct will comprise at least two or at least three repeats of bases of the first 1745 bases of the promoter of SEQ ID NO: 10. In an embodiment one or two copies are upstream from a globulin-1 promoter. The enhanced promoter will include a transcription start site including a translation start site. The transcription start site can vary as to the particular sequence and is that region in which transcription of the RNA begins; the translation start site is ATG. The transcription start site in the example is the first nucleotide of SEQ ID NO: 13, is the first nucleotide of SEQ ID NO: 8 in the extended globulin-1 leader and is the first nucleotide of SEQ ID NO: 5 in the globulin-1 UTR.

The enhanced promoter will include at least one additional copy and in another embodiment at least two copies upstream of a globulin-1 promoter which comprises the globulin-1 regulatory region or fragmeneter thereof, which comprises at least one transcription factor binding domain. Transcription factors bind specific DNA sequences and control transcription of DNA to mRNA. These are proteins that bind upstream of the transcription start site and regulate expression through inhibition or activation of the transcription process. A vast array of transcription factor binding domains are known. See, eg., Veerla et al. (2010) "Genome-wide transcription factor binding site/promoter databases for the analysis of gene sets and co-occurrence of transcription factor binding motifs" *BMC Genomics* 11:145. In fact a number of databases are available for transcription factors and domains, including those specific to plants. See, e.g., Wingender et al. (1996) "TRANSFAC: a database on transcription factors and their DNA binding sites" *Nucleic Acids Research* Vol. 24, No. 1 pp. 238-241; Sandelin et al. (2004) "JASPAR: an open-access database for eukaryotic transcription factor binding profiles" *Nucleic Acids Research* Vol. 32, Database issue D91-D94; DOI: 10/1093/nar/gkh012; "Plant promoter and Regulatory Element Resources—DATF: Database of *Arabidopsis* Transcription Factors" provided by The *Arabidopsis* Information Resource (TAIR) through the *Arabidopsis* Biological Resource Center at Ohio State University, at www.arabidopsis.org/portals/genAnnotation/genome_annotation_tools/cis_element.jsp Such regions can be identified by various means including identification of motifs that may be about 10 bp or less. Various bioinformatics approaches can also be used to identify such sites. See, e.g., Catharius et al. (2005) *Bioinformatics* Vol. 21 No. 13, pp. 2933-2941; Donaldson et al. (2005) *Bioinformatics* Vol. 21 No. 13, pp. 3058-3059.

Clearly, one skilled in the art appreciates there can be variations in the regulatory region tolerated and still produce the increased expression described. The repeat promoter of the invention thus will include the extended globulin-1 binding domain regions, the initiation start site and a translation start site yet tolerate variation in any additional sequences provided. While at the same time preserving at least one transcriptional binding site, some range of identity of the regulatory region, if used in the construct, is within the scope of the subject invention. Identity to the sequence of the present invention can be a polynucleotide sequence having at least 65% sequence identity, more preferably at least 70% sequence identity, more preferably at least 75% sequence identity, more preferably at least 80% identity, and more preferably at least 85% 86%, 87%, 88%, 89%, 90%, 91%, 92%, 93%, 94%, 95%, 96%, 97%, 98%, 99% sequence identity with a sequence exemplified or described herein. Hybridization and hybridization conditions as provided herein can also be used to define polynucleotide sequences of the invention.

The construct may comprise further regions of the extended globulin-1 or globulin-1 promoter, but will comprise at least one or at least two repeats upstream of the promoter, where the repeats comprise at least one transcriptional binding domain. For example, the construct may or may not include the untranslated leader. Further, other regulatory regions may be included as desired in the construct. Examples of a globulin-1 promoter include SEQ ID NO: 3 and the extended globulin-1 promoter of SEQ ID NO: 6. By way of example, without limitation, the repeated region may comprise a fragment of SEQ ID NO: 3, 4, 6, 7 or 10 which comprises a transcriptional binding domain; or may be the 1745 bases of SEQ ID NO: 10. In another example, the construct may comprise SEQ ID NO: 12 and one or two copies of SEQ ID NO: 10. Examples of transcriptional binding domains discussed in the examples below and include for example, any one of SEQ ID NOs: 16-30.

The promoter is particularly useful for the expression of gene sequences in cereal plants and especially in maize plants. However, it can be used in any plant species, including, for example, a monocotyledonous plant such as wheat, rye, rice, oat, barley, turfgrass, sorghum, millet or sugarcane. Alternatively, the plant may be a dicotyledonous plant, for example, tobacco, tomato, potato, soybean, cotton, canola, sunflower or alfalfa. Maize promoters have been used repeatedly to drive expression of genes in non-maize plants, including tobacco (Yang and Russell, 1990; Geffers et al., 2000; Vilardell et al., 1991), cultured rice cells (Vilardell et al., 1991), wheat (Oldach et al., 2001; Brinch-Pedersen et al., 2003), rice (Cornejo et al., 1993; Takimoto et al., 1994), sunflower (Roussell et al., 1988) and protoplasts of carrot (Roussell et al., 1988).

The nucleotide sequences of the invention can be used to isolate corresponding sequences from other organisms, particularly other plants, more particularly other monocots, or to synthesize synthetic sequences. In this manner, methods such as PCR, hybridization, synthetic gene construction and the like can be used to identify or generate such sequences based on their sequence homology to the sequences set forth herein. Sequences identified, isolated or constructed based on their sequence identity to the whole of or any portion of the maize extended globulin-1 or globulin-1 promoter of SEQ ID NO: 4 or 10, which may include the untranslated leader sequences set forth herein, may be used in the present invention. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook et al., 1989; Innis et al., 1990; Innis et al., 1995; Innis et al., 1999). Known methods of PCR include, but are not limited to, methods using paired primers, nested primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989).

For example, the extended globulin-1 or globulin-1 promoter that may include the untranslated leader sequence disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989).

Hybridization of such sequences may be carried out under stringent conditions. By “stringent conditions” or “stringent hybridization conditions” is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1.0 M NaCl, 1% SDS at 37° C., and a wash in 0.1×SSC at 60 to 65° C.

Specificity is also the function of post-hybridization washes, the critical factors being the ionic strength and temperature of the final wash solution. For DNA-DNA hybrids, the $T_m$ can be approximated from the equation $T_m$=81.5° C.+16.6(log M)+0.41(% GC)−0.61(% form.)−500/L, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Ausubel et al. (1993) and Sambrook et al. (1989).

Thus, isolated sequences that have promoter activity and which hybridize under stringent conditions to the promoter sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches. Methods of alignment of sequences for comparison are well known in the art. Thus, the determination of percent identity between any two sequences can be accomplished using a mathematical algorithm. Optimal alignment of sequences for comparison can use any means to analyze sequence identity (homology) known in the art, e.g., by the progressive alignment method of termed "PILEUP" (Morrison, Mol. Biol. Evol. 14:428-441 (1997), as an example of the use of PILEUP); by the local homology algorithm of Smith & Waterman (Adv. Appl. Math. 2: 482 (1981)); by the homology alignment algorithm of Needleman & Wunsch (J. Mol. Biol. 48:443 (1970)); by the search for similarity method of Pearson (Proc. Natl. Acad. Sci. USA 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins, Gene 73: 237-244 (1988); Corpet, Nucleic Acids Res. 16:10881-10890 (1988); Huang, Computer Applications in the Biosciences 8:155-165 (1992); and Pearson, Methods in Mol. Biol. 24:307-331 (1994); Pfam (Sonnhammer, Nucleic Acids Res. 26:322-325 (1998); TreeAlign (Hein, Methods Mol. Biol. 25:349-364 (1994); MEG-ALIGN, and SAM sequence alignment computer programs; or, by manual visual inspection.

Another example of an algorithm that is suitable for determining sequence similarity is the BLAST® algorithm, which is described in Altschul et al, J. Mol. Biol.215: 403-410 (1990). The BLAST programs (Basic Local Alignment Search Tool) of Altschul, S. F., et al., (1993) J. Mol. Biol. 215:403-410) searches under default parameters for identity to sequences contained in the BLAST® "GEN-EMBL" database. A sequence can be analyzed for identity to all publicly available DNA sequences contained in the GENEMBL database using the BLASTN algorithm under the default parameters.

Software for performing BLAST® analyses is publicly available through the National Center for Biotechnology Information, www.ncbi.nlm.nih.gov/; see also Zhang, Genome Res. 7:649-656 (1997) for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al, J. Mol. Biol. 215: 403-410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® algorithm parameters W, T and X determine the sensitivity and speed of the alignment. The BLAST® program uses as defaults a wordlength (W) of 11, the BLOSUM62 scoring matrix (see Henikoff, Proc. Natl. Acad. Sci. USA 89:10915-10919 (1992)) alignments (B) of 50, expectation (E) of 10, M=5, N=−4, and a comparison of both strands. The term BLAST® refers to the BLAST® algorithm that performs a statistical analysis of the similarity between two sequences; see, e.g., Karlin, Proc. Natl. Acad. Sci. USA 90:5873-5787 (1993). One measure of similarity provided by the BLAST® algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. In an embodiment, GAP (Global Alignment Program) can be used. GAP uses the algorithm of Needleman and Wunsch J. Mol. Biol. 48:443-453 (1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff, Proteins, 17: 49-61 (1993)), which is currently the default choice for BLAST programs. BLOSUM62 uses a combination of three matrices to cover all contingencies. Altschul, J. Mol. Biol. 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) Proc. Natl. Acad. Sci. USA 89:10915). As used herein, "sequence identity" or "identity" in the context of two nucleic acid sequences makes reference to the residues in the two sequences that are the same when aligned for maximum correspondence over a specified comparison window. As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to a sequence of the present invention would mean a polynucleotide or amino acid sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

The invention is further to "functional variants" of the regulatory sequence disclosed. Functional variants include, for example, regulatory sequences of the invention having one or more nucleotide substitutions, deletions or insertions and wherein the variant retains promoter activity, particularly the ability to drive expression preferentially to the embryo of a plant. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of reporter activity as is described at U.S. Pat. No. 6,844,484, Northern blot analysis or similar techniques. The '484 patent describes the identification of functional variants of different promoters.

The invention further encompasses a "functional fragment" that is a regulatory fragment formed by one or more deletions from a larger regulatory element. For example, the 5' portion of a promoter up to the TATA box near the transcription start site can be deleted without abolishing promoter activity, as described by Opsahl-Sorteberg, H-G. et al., 2004. Such fragments should retain promoter activity, particularly the ability to drive expression of operably linked nucleotide sequences. Activity can be measured by Northern blot analysis, reporter activity measurements when using transcriptional fusions, and the like. See for example, Sambrook et al. (1989). Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology. See particularly, Mullis et al. (1987) and Erlich, ed. (1989).

For example, a routine way to remove a part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at the 5' overhangs, blunt ends or nicks in the DNA template. However, the exonuclease III is unable to remove nucleotides at 3' 4-base overhangs. Timed digest of a clone with this enzyme produces unidirectional nested deletions.

The promoter of the invention may be combined with any number of other components to be introduced into the plant, including combined with a gene of interest to be expressed in the plant. The "gene of interest" refers to a nucleotide sequence that encodes for a desired polypeptide or protein but also may refer to nucleotide sequences that do not constitute an entire gene, and which do not necessarily encode a polypeptide or protein. For example, when used in a homologous recombination process, the promoter may be placed in a construct with a sequence that targets an area of the chromosome in the plant but may not encode a protein. The promoter can be used to drive mRNA that can be used for a silencing system, such as antisense, and in that instance, no protein is produced. Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required.

In an example, the gene of interest may encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. The sequences used with the promoter can be native or non-native sequences to the plant. DNA sequences native to plants as well as non-native DNA sequences can be transformed into plants and used to modulate levels of native or non-native proteins.

Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene (such as the promoter of the invention or another promoter); and DNA elements that control the processing of transcripts, such as transcription termination/polyadenylation sequences. It also can contain such sequences as are needed for the eventual integration of the vector into the plant chromosome.

Clearly, many variations in use of the promoter of the invention are available to one skilled in the art.

If desired, a nucleic acid molecule can be optimized for plant translation by optimizing the codons used for plants and the sequence around the translational start site for plants. Sequences resulting in potential mRNA instability can also be avoided. See, for example, Campbell and Gowri (1990) Plant Physiol. 92: 1-11 for a discussion of host-preferred codon usage. Methods are available in the art for synthesizing plant-preferred genes. See, for example, U.S. Pat. Nos. 5,380,831, 5,436,391, and Murray et al. (1989) Nucl. Acids Res. 17:477-498 (1989). Additional sequence modifications are known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

A heterologous polynucleotide or a heterologous nucleic acid or an exogenous DNA segment refers to a polynucleotide, nucleic acid or DNA segment that originates from a source foreign to the particular host cell, or, if from the same source, is modified from its original form in composition and/or genomic locus by human intervention. A heterologous gene in a host cell includes a gene that is endogenous to the particular host cell, but has been modified or introduced into the plant. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription and in a desired manner. When referring to preferential expression, what is meant is expression at a higher level in the particular plant tissue than in other plant tissue. The present regulatory region confers expression preferentially in the embryo. When referring to an embryo preferred promoter is meant that it expresses an operably linked sequence to a higher degree in embryo tissue than in other plant tissue. It may express during embryo development, along with expression at other stages, may express strongly during embryo development and to a much lesser degree at other times.

The promoter of the invention may also be used in conjunction with another promoter. In one embodiment, the plant selection marker and the gene of interest can be both functionally linked to the same promoter. In another embodiment, the plant selection marker and the gene of interest can be functionally linked to different promoters. In yet third and fourth embodiments, the expression vector can contain two or more genes of interest that can be linked to the same promoter or different promoters. For example, the enhanced globulin-1 promoter described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, the ubiquitin promoter (European patent application no. 0 342 926); the promoter for the small subunit of ribulose-1,5-bis-phosphate carboxylase (ssRUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten and Schell, 1985) that have plant activity; or viral promoters such as the cauliflower mosaic virus (CaMV) 19S and 35S promoters (Guilley et al., 1982; Odell et al., 1985), the figwort mosaic virus FLt promoter (Maiti et al., 1997) or the coat protein promoter of TMV (Grdzelishvili et al., 2000). Alternatively, plant promoters such as heat shock promoters for example soybean hsp 17.5-E (Gurley et al., 1986); or ethanol-inducible promoters (Caddick et al., 1998) may be used. See International Patent Application No. WO 91/19806 for a review of illustrative plant promoters suitably employed in the present invention.

A promoter can additionally comprise other recognition sequences generally positioned upstream or 5' to the TATA box, referred to as upstream promoter elements, which influence the transcription initiation rate. It is recognized that having identified the nucleotide sequences for the promoter region disclosed herein, it is within the state of the art to isolate and identify further regulatory elements in the 5' region upstream from the particular promoter region identified herein. Thus the promoter region disclosed herein is generally further defined by comprising upstream regulatory elements such as those responsible for tissue and temporal expression of the coding sequence, enhancers and the like. In the same manner, the promoter elements which enable expression in the desired tissue such as the embryo can be identified, isolated, and used with other core promoters to confirm embryo-preferred expression. By core promoter is meant the sequence sometimes referred to as the TATA box (or similar sequence) which is common to promoters in all genes encoding proteins. Thus the upstream promoter of globulin-1 can optionally be used in conjunction with its own or core promoters from other sources.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989).

In addition to a promoter, the expression cassette can include one or more enhancers. By "enhancer" is intended a cis-acting sequence that increases the utilization of a promoter. Such enhancers can be native to a gene or from a heterologous gene. Further, it is recognized that some promoters can contain one or more enhancers or enhancer-like elements. An example of one such enhancer is the 35S enhancer, which can be a single enhancer, or duplicated. See for example, McPherson et al, U.S. Pat. No. 5,322,938. Other methods known to enhance translation can also be utilized, for example, introns, and the like. Other modifications can improve expression, include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In one embodiment, the expression vector also contains a gene encoding a selectable or scoreable marker that is operably or functionally linked to a promoter that controls transcription initiation, which can be the promoter of the invention or another promoter. By "operably linked" it is understood that the gene of interest when it is placed into a functional relationship with another nucleic acid segment. In this case the gene encoding a selectable or scoreable marker is oriented in connection to the gene such that the promoter initiates transcription of the gene in order to allow its expression of the resulting protein in plants. In another example, DNA for a signal sequence is operably linked to DNA encoding a polypeptide if it is expressed as a preprotein that participates in secretion of the polypeptide. Operably linked elements may be contiguous or non-contiguous. When used to refer to the joining of two protein coding regions, the coding regions are in the same reading frame. Alternatively, the additional gene(s) can be provided with a pluralirty of restriction sites and/or recombination sites for insertion of the polynucleotide to be under the transcriptional regulation of the regulatory regions. For a general description of plant expression vectors and reporter genes, see Gruber et al. (1993). In one embodiment, the selective gene is a glufosinate-resistance encoding DNA and in another embodiment it can be phosphinothricin acetyl transferase (pat) or a maize optimized pat gene under the control of the CaMV 35S promoter. Such pat genes confer resistance to the herbicide bialaphos (Gordon-Kamm et al., 1990).

The expression vector can optionally also contain a signal sequence located between the promoter and the gene of interest. A signal sequence is a nucleotide sequence, translated to give an amino acid sequence, which is used by a cell to direct the protein or polypeptide of interest to be placed in a particular place within or outside the eukaryotic cell. One example of a plant signal sequence is the barley α-amylase secretion signal (Rogers, 1985). Many signal sequences are known in the art. See, for example Becker et al. (1992), Fontes et al. (1991), Matsuoka and Nakamura (1991), Gould et al. (1989), Creissen et al. (1992), Kalderon et al. (1984) and Stiefel et al. (1990).

Leader sequences can be included to enhance translation. Instead of, or in addition to the untranslated leader sequence of the globulin-1 promoter, other leader sequences may be substituted or added. Translation leaders are known in the art and include: picornavirus leaders, for example, EMCV leader (Encephalomyocarditis 5' noncoding region) (Elroy-Stein et al. (1989); potyvirus leaders, for example, TEV leader (Tobacco Etch Virus) (Gallie et al. (1995)); human immunoglobulin heavy-chain binding protein (BiP) (Macejak et al. (1991)); untranslated leader from the coat protein mRNA of alfalfa mosaic virus (AMV RNA 4) (Jobling et al. (1987)); tobacco mosaic virus leader (TMV) (Gallie. (1989)); and maize chlorotic mottle virus leader (MCMV) (Lommel et al. (1991)). See also, Della-Cioppa et al. (1987). Other methods known to enhance translation can also be utilized, for example, introns, and the like. Obviously, many variations on the promoters, selectable markers, signal sequences, leader sequences, termination sequences, introns, enhancers and other components of the construct are available to one skilled in the art.

Methods for introducing expression vectors into plant tissue available to one skilled in the art are varied and will depend on the plant selected. Procedures for transforming a wide variety of plant species are well known and described throughout the literature. See, for example, Miki and McHugh (2004); Klein et al. (1992); and Weising et al. (1988). For example, the DNA construct may be introduced into the genomic DNA of the plant cell using techniques such as microprojectile-mediated delivery (Klein et al. 1992), electroporation (Fromm et al., 1985), polyethylene glycol (PEG) precipitation (Mathur and Koncz, 1998), direct gene transfer (WO 85/01856 and EP-A-275 069), in vitro protoplast transformation (U.S. Pat. No. 4,684,611) and microinjection of plant cell protoplasts or embryogenic callus (Crossway, 1985). Co-cultivation of plant tissue with *Agrobacterium tumefaciens* is another option, where the DNA constructs are placed into a binary vector system (Ishida et al., 1996). The virulence functions of the *Agrobacterium tumefaciens* host will direct the insertion of the construct into the plant cell DNA when the cell is infected by the bacteria. See, for example, Fraley et al. (1983).

Standard methods for transformation of canola are described by Moloney et al. (1989). Corn transformation is described by Fromm et al. (1990) and Gordon-Kamm et al. (1990). *Agrobacterium* is primarily used in dicots, but certain monocots such as maize can be transformed by *Agrobacterium*. See, for example, U.S. Pat. No. 5,550,318. Rice transformation is described by Hiei et al. (1994) and Lee et al. (1991). Wheat can be transformed by techniques similar to those used for transforming corn or rice. *Sorghum* transformation is described by Casas et al. (1993) and barley transformation is described by Wan and Lemaux (1994).

Soybean transformation is described in a number of publications, including U.S. Pat. No. 5,015,580.

In one preferred method, the *Agrobacterium* transformation methods of Ishida et al. (1996) and also described in U.S. Pat. No. 5,591,616, are generally followed, with modifications that the inventors have found improve the number of transformants obtained. The Ishida method uses the A188 variety of maize that produces Type I callus in culture. In one preferred embodiment the Hi II maize line is used which initiates Type II embryogenic callus in culture (Armstrong et al., 1991).

While Ishida recommends selection on phosphinothricin when using the bar or pat gene for selection, another preferred embodiment provides use of bialaphos instead. In general, as set forth in U.S. Pat. No. 5,591,616, and as outlined in more detail below, dedifferentiation is obtained by culturing an explant of the plant on a dedifferentiation-inducing medium for not less than seven days, and the tissue during or after dedifferentiation is contacted with *Agrobacterium* having the gene of interest. The cultured tissue can be callus, an adventitious embryo-like tissue or suspension cells, for example. In this preferred embodiment, the suspension of *Agrobacterium* has a cell population of $10^6$ to $10^{11}$ cells/ml and are contacted for three to ten minutes with the tissue, or continuously cultured with *Agrobacterium* for not less than seven days. The *Agrobacterium* can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986).

Further, the Ishida protocol as described provides for growing fresh culture of the *Agrobacterium* on plates, scraping the bacteria from the plates, and resuspending in the co-culture medium as stated in U.S. Pat. No. 5,591,616 for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase, and are harvested at a density of no more than $OD_{600}$=0.5, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985). The resuspension medium is the same as that described above. All further Hi II media are as described in Armstrong and Green (1985). The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

In accordance with the present invention, a transgenic plant is produced that contains an introduced enhanced globulin-1 promoter. It can be combined with any one of the components set forth above. In a preferred embodiment, the promoter is driving expression of a nucleotide sequence such that the sequence encodes a protein preferentially expressed in the seed of the plant.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants, and selection for plants from subsequent generations which express the amino acid sequence. The plant breeding methods used herein are well known to one skilled in the art. For a discussion of plant breeding techniques, see Poehlman and Sleper (1995). Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detassling, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Neal (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

EXAMPLES

The following is presented as illustrative of an embodiment of the invention and is not intended to limit the scope of the invention as otherwise set forth.

Example 1

Production of the Extended Globulin-1 Promoter

Materials and Methods

Construction of cDNA Libraries Representative of Maize Embryo Tissues

Maize plants were grown from seed in moist soil under standard greenhouse conditions. Four lines of maize were grown, representative Lancaster, Stiff Stalk, high protein and high oil lines. Elite inbreds are commonly derived from germplasm pools known as Stiff Stalk and Lancaster. Stiff Stalk inbreds have been known for decades and are reported by the USDA to have been widely available for decades. They are derived from the Iowa Stiff Stalk synthetic population (Sprague, 1946). For example see PI accession no. 550481 and discussions of Stiff Stalk germplasm at U.S. Pat. Nos. 5,706,603; 6,252,148; 6,245,975; 6,344,599 and 5,134,074. See also, Neuhausen (1989). Lancaster inbreds are derived from the open pollinated variety Lancaster Surecrop (Anderson, 1944). See for example, PI 280061. High oil or high protein plants are those in which the oil or protein content of the seed is higher than lower oil or protein producing plants such as hybrid #2 yellow dent corn.

Plants were self-pollinated and individual plants were sacrificed at 10, 11, 12, 19, 28, 37 and 46 days post-pollination. Embryos were immediately harvested from these plants, frozen in liquid nitrogen and stored at −80° C. Embryos harvested from distinct lines and at different time points were kept separate, except that embryos of the same line harvested at 10, 11 and 12 days post-pollination were pooled. For each of the five resulting time points (10 to 12 days, 19 days, 28 days, 37 days and 46 days post-pollination) equal amounts of embryo tissues harvested from each of the four maize lines were pooled. Total RNA was isolated from the pooled embryo tissues using a phenol-based method (Chatterjee et al., 1996), and poly-A message was then prepared from this RNA using Poly(A) Quik mRNA isolation columns (Stratagene; La Jolla, Calif.). These poly-A RNA samples were used to prepare five cDNA libraries, each representative of all four maize lines and each corresponding to a different time point of embryo development. The libraries were constructed in the Lambda ZAP II vector (Stratagene; La Jolla, Calif.).

DNA Sequence Analysis of Representative Clones from Maize Embryo Libraries

For each of the five libraries, phagemids were excised from the phage vector. Approximately 100 clones were randomly selected to represent each library and the nucleotide sequences of the cDNA inserts were determined using the chain termination approach using attached dyes by the 'DNA Sequencing and Synthesis Facility' of Iowa State University (Ames, Iowa). Nucleotide sequences of clones were compared using the 'Sequencher™' package (Gene Codes Corporation; Ann Arbor, Mich.).

Analysis of Clone Representation in Embryo Libraries by Plaque Hybridization

Equal aliquots of each of the five embryo developmental time point cDNA libraries were pooled, and the pooled phage infected onto the bacterial strain XL1-Blue MRF' (Stratagene; La Jolla, Calif.) to generate approximately 30,000 plaques upon plating. Phage DNA was transferred onto charged nylon filters (Amersham; Piscataway, N.J.) and cross-linked to the filters by exposure to ultraviolet light. Radionucleotide ($^{32}P$) was incorporated into globulin-1 cDNA sequence by random prime labeling (Feinberg and Vogelstein, 1983) using the 'High Prime' reagent mix (Roche Diagnostics GmbH; Mannheim, Germany) and the filters were incubated with this probe. Filters were washed under conditions of high stringency (15 mM NaCl, 1.5 mM sodium citrate [$Na_3C_6H_5O_7.2H_2O$], 0.1% sodium dodecyl sulfate, 65° C.) and exposed to BioMax MS film (Kodak; Rochester, N.Y.), to reveal clones homologous to globulin-1 cDNA.

Analysis of Genome Organization by DNA Hybridization

DNA was prepared from maize leaves using a hexadecyltrimethyl-ammonium bromide based method (Stacey and Issac, 1994). DNA (15 μg samples) was digested with the restriction endonucleases EcoRI or HindIII and DNA fragments were size separated on 0.7% agarose gels. Vector DNA was similarly digested and 60 pg was size separated on the gels. The DNA was transferred onto charged nylon filters (Amersham; Piscataway, N.J.) and cross-linked to the filters by exposure to ultraviolet light. Radionucleotide ($^{32}P$) was incorporated into globulin-1 cDNA sequence by random prime labeling using the 'High Prime' reagent mix (Roche Diagnostics GmbH; Mannheim, Germany) and the filters were incubated with this probe. Filters were washed under conditions of high stringency (15 mM NaCl, 1.5 mM sodium citrate [$Na_3C_6H_5O_7.2H_2O$], 0.1% sodium dodecyl sulfate, 65° C.) and exposed to BioMax MS film (Kodak; Rochester, N.Y.).

Analysis of Message Levels by RNA Hybridization

Total RNA was isolated from maize tissues using a phenol-based method (Chatterjee et al., 1996). RNA (20 μg samples) was size separated on agarose/formaldehyde gels, transferred onto charged nylon filters (Amersham; Piscataway, N.J.) and cross-linked to the filters by exposure to ultraviolet light. Radionucleotide labeled DNA probes were prepared by random prime labeling using the 'High Prime' reagent mix (Roche Diagnostics GmbH; Mannheim, Germany) and the filters were incubated with maize globulin-1 cDNA or 18S rRNA gene sequences. Filters were washed under conditions of high stringency (15 mM NaCl, 1.5 mM Na$_3$C$_6$H$_5$O$_7$.2H$_2$O, 0.1% sodium dodecyl sulfate, 65° C.) and exposed to BioMax MS film (Kodak; Rochester, N.Y.). DNA probes were stripped from filters by washing with near-boiling 0.1% sodium dodecyl sulfate.

Cloning of And Nucleotide Sequence Determination of An Improved Globulin-1 Promoter DNA sequences upstream of a globulin-1 open reading frame were isolated from a maize Missouri-13 line genomic library in the Lambda FIX II vector (Stratagene; La Jolla, Calif.). The phage library was infected onto the bacterial strain XL1-Blue MRA (Stratagene; La Jolla, Calif.) and plated to generate plaques. Phage DNA was transferred onto charged nylon filters (Amersham; Piscataway, N.J.) and cross-linked to the filters by exposure to ultraviolet light. Radionucleotide ($^{32}$P) was incorporated into globulin-1 cDNA sequence by random prime labeling using the 'High Prime' reagent mix (Roche Diagnostics GmbH; Mannheim, Germany) and the filters were incubated with this probe. Filters were washed under conditions of high stringency (15 mM NaCl, 1.5 mM sodium citrate [Na$_3$C$_6$H$_5$O$_7$.2H$_2$O], 0.1% sodium dodecyl sulfate, 65° C.) and exposed to BioMax MS film (Kodak; Rochester, N.Y.) to reveal sequences homologous to globulin-1 cDNA. Homologous clones were recovered and the phage inserts mapped by comparing restriction endonuclease digests of the clones following size fractionation via agarose gel electrophoresis.

The nucleotide sequence of DNA identified as extending approximately 3 kb 5' of globulin-1 open reading frame sequence was determined by the 'DNA Sequencing Facility' of Iowa State University (Ames, Iowa). The sequence is shown in FIG. 3. The untranslated leader is in bold and translation start codon capitalized. The entire sequence is SEQ ID NO: 6, the promoter is SEQ ID NO: 7 and the untranslated leader is SEQ ID NO: 8. Construct of promoter-report gene fusions, introduction into plants and analysis of expression is describe at patent '967 and in particular at columns 14-28, incorporated herein by reference.

Example 2

The Enhanced Globulin-1 Regulatory Region

The first 1745 bases (SEQ ID NO: 10) of the extended globulin-1 regulatory sequence (SEQ ID NO: 6) were used as the repeat region of the enhanced globulin-1 regulatory region. FIG. 4A-C shows the sequences of an enhanced globulin-1 regulatory region construct including restriction sites and signal sequences used in the experiments described below (SEQ ID NO: 9).

Two types of putative sequence transcriptional binding elements were identified in the extended globulin-1 promoter, the RY-repeat/SphI element, and the ABRE element. Based on this evidence, the extended region upstream of the HindIII site was PCR amplified and repeated in tandem three times.

RY-repeat/SphI Element

Within the extended globulin promoter upstream of the HindIII site there are 10 putative RY-repeat/Sph element sequences. They contain three or fewer mismatches to the most conserved region of the sequence described in Hattori et al, 1992, *Genes and Development* Vol. 6, p. 609-618 (sequence is TC<u>CATGCATGC</u>AC (SEQ ID NO: 16), with the most conserved sequence underlined). Binding regions in common with all three repeats are identified here. All putative RY-repeat/Sph sequences are marked in bold, upper case, underlined characters in FIG. 4A-C and elements 1 to 10 are listed 5' to 3' below (most conserved sequence underlined, mismatches in bold below). Coordinates of the binding sites found at the identified bases of the enhanced globulin-1 regulatory region of SEQ ID NO: 9 are shown. "Consensus sequence" disclosed as SEQ ID NO: 16.

```
Consensus seq:    TCCATGCATGCAC    Coordinates

Sph element 1:    TTTATGCATTA      3583-3593  (SEQ ID NO: 17)

Sph element 2:    TATGCTTGAA       3616-3625  (SEQ ID NO: 18)

Sph element 3:    TATGCATGT        3638-3646  (SEQ ID NO: 19)

Sph element 4:    TTCATGCTTTCA     3791-3802  (SEQ ID NO: 20)

Sph element 5:    TACCAGCATGAA     4058-4069  (SEQ ID NO: 21)

Sph element 6:    CATGAATGCA       4064-4073  (SEQ ID NO: 22)

Sph element 7:    TTCATGTATGAA     4132-4143  (SEQ ID NO: 23)

Sph element 8:    GAGGCATGAAC      4376-4386  (SEQ ID NO: 24)

Sph element 9:    CATGCGTTTA       4501-4510  (SEQ ID NO: 25)

Sph element 10:   CCTGCAAGGA       4773-4782  (SEQ ID NO: 26)
Note:
-Putative Sph elements 5 and 6 overlap in sequence
ABBE element
```

Within the extended globulin promoter upstream of the HindIII site, there are also putative ABRE sites. The consensus sequence in rice is <u>ACGTG</u>(G/T)C (SEQ ID NO: 27) (described in Hattori et al, 2002, *Plant and Cell Physiology*, 43(1) p. 136-140) and in *Arabidopsis* is (C/G/T)<u>ACGTG</u>(G/T)(A/C) (SEQ ID NO: 28) (described in Chen 2002, *Plant Cell*, 14:559. The putative ABRE sequences in the extended globulin promoter are in bold, upper case, underlined italics in FIG. 4 and coordinates at bases of SEQ ID NO: 9 are shown below. Putative ABRE sites were defined as having one or fewer mismatches within the most conserved portion of the ABRE sequence. The *Arabidopsis* sequence was used for comparison beyond the core consensus (core underlined, mismatches in /bold below). "Consensus sequence" disclosed as SEQ ID NO: 28.

```
Consensus seq:   (C/G/T)ACGTG(G/T)(A/C)  Coordinates
ABRE element 1:  CACGTT                  4163-4168 (SEQ ID NO: 29)
ABRE element 2:  GACGTC                  4491-4496 (SEQ ID NO: 30)
```

Within SEQ ID NO: 9, several features are included. Bases 1-8 are the AscI restriction enzyme site (site indicated with tildes above the nucleotide sequence). Bases 8-1752 are the first repeat, bases 1759-3503 are the second repeat, and bases 3510-5254 are the third repeat of the 1745 fragment of the promoter which comprise at least one transcriptional binding site and is SEQ ID NO: 10 (note in the first repeat, the first C is both part of the promoter repeat and also the last base pair of the AscI site). The first two repeats are upstream of, and the third repeat is contained within, the extended globulin-1 promoter of bases 3510-6512 (SEQ ID NO: 11). This extended globulin-1 promoter is the same as that of the '967 patent except that base 6512, just before the ATG start codon, is C instead of G. The first and third repeats are underlined. The non-repeat region of the globulin-1 promoter is bases 5255-6459 (SEQ ID NO: 12). The TATA box is at bases 6427-6433 (in italics). The transcription initiation site is base 6460 and the leader sequence is bases 6460-6512, shown in bold (SEQ ID NO: 13). AscI/MluI sites were joined at bases 1753-1759 and 3504-3510 (indicated by italics) and these regions are not a part of the promoter but artifacts of producing the construct.

Additional sequences are shown in FIG. 4 A-C used to create the plasmids used in the experiments below. A HindIII site is at bases 5255-5260 and is not a part of the promoter but an artifact of producing the construct (indicated by tildes above the nucleotides comprising the restriction site). The barley alpha amylase signal sequence (BAASS) is bases 6513-6584. (SEQ ID NO: 14). The hepatitis B surface antigen sequence was optimized from GenBank® accession number 562754 shown bases 6585-7262 in italics (bold and italics) (SEQ ID NO: 15). The BAASS:hepatitis B start codon is at bases 6513-6515 and stop codon at bases 7260-7263 (lower case). The NcoI restriction site is bases 6511-6516 (indicated by tildes above the nucleotides comprising the restriction site) and the first two bases (CC) are part of the promoter.

Example 3

Preparation of Constructs

The Hepatitis B surface antigen (HBsAg) sequence, identical to the surface antigen protein sequence available in GenBank® accession 562754.1 (adr subtype, small form i.e. S open reading frame without pre-S1 or pre-S2 sequences), was engineered to be codon optimized for expression in maize in all of the above constructs. (See FIG. 4C, bases 6585-7262, SEQ ID NO: 15). At the N-terminus a cell-wall targeting sequence, the barley alpha amylase signal sequence, (Rogers, J. C. (1985) "Two barley alpha-amylase gene families are regulated differently in aleurone cells" *J. Biol. Chem.* 260, 3731 3738; See FIG. 4C, bases 6513-6584, SEQ ID NO: 14) was fused to HBsAg in order to produce maximally-expressing lines. All HBsAg constructs were built to contain a pin II (potato proteinase inhibitor II) termination sequence (An, et al. (1989) "Functional analysis of the 3' control region of the potato wound-inducible proteinase inhibitor II gene" *Plant Cell* 1, 115 122). Differences among the constructs were generated at the promoter sequence level.

HBE uses the globulin-1 promoter of Belanger et al., supra, of GenBank® accession No. L22344 (SEQ ID NO: 4). In the version used in these experiments an extra 43 bases followed the promoter (shown in FIG. 2 in bold below the promoter and which is SEQ ID NO: 31). These extra bases are not relevant to the promoter and believed to be a downstream portion on chromosome 1 of the maize gene, which may originate from a retrotransposon. A selectable marker employed in the construct is the maize optimized PAT sequence providing resistance to the herbicide glufosinate. See, Gordon-Kamm et al., (1990) *Plant Cell* 2:603; Uchimiya et al., (1993) *BioTechnology* 11:835; White et al., *Nucl. Acids Res.* 18:1062, (1990); Spencer et al., 1990) *Theor. Appl. Genet.* 79:625-631, and Anzai et al., (1989) *Mol. Gen. Gen.* 219:492. A version of the PAT gene is the maize optimized PAT gene, described at U.S. Pat. No. 6,096,947. The resulting plasmid HBE map is shown in FIG. 5.

Figure 6:
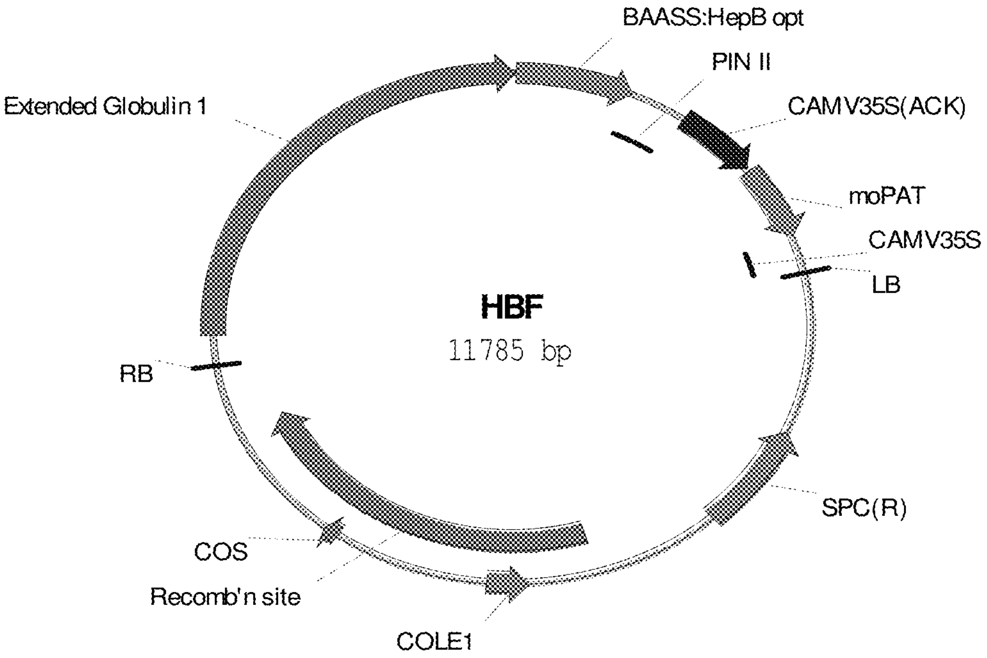
FIG. 6 is a map of plasmid HBF used in the experiments below.

HBF: uses the extended globulin-1 promoter of U.S. Pat. No. 7,169,967, incorporated herein by reference, and seen in FIG. 3, SEQ ID NO: 6, with sequence modification as described for SEQ ID NO: 11. The Plasmid map is shown in FIG. 6.

Figure 7:
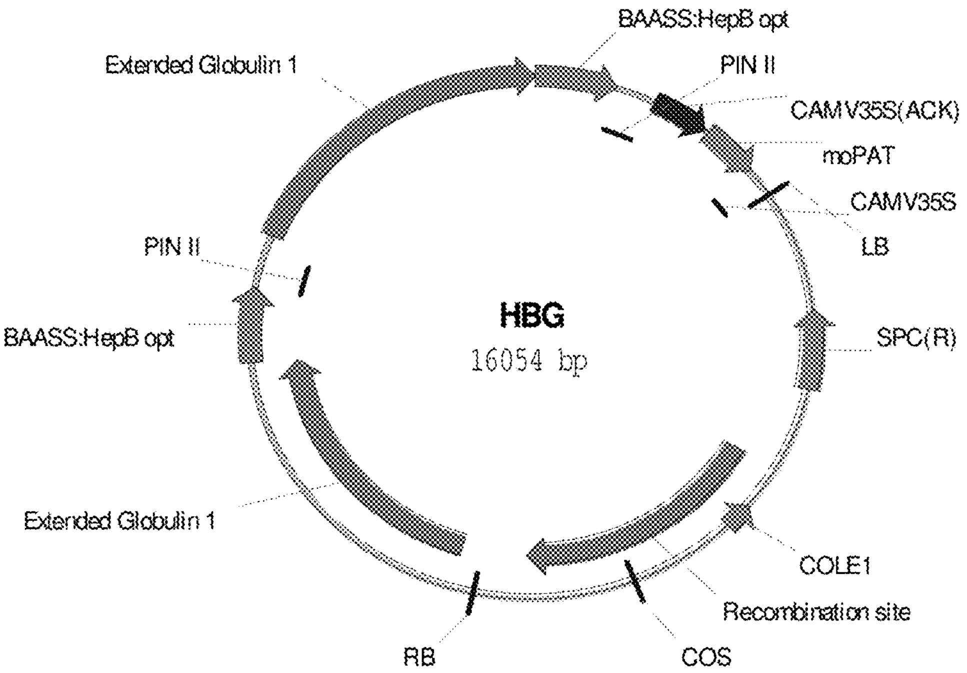
FIG. 7 is a map of plasmid HBG used in the experiments below.
Figure 7A:
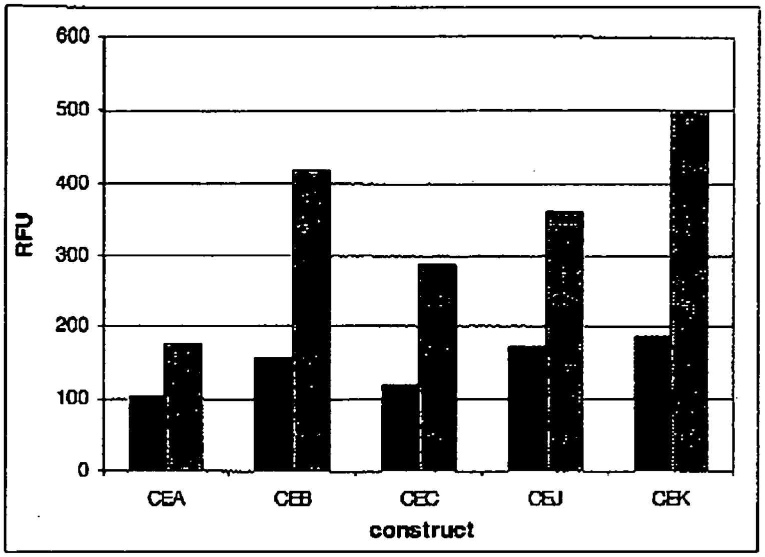
Figure 7B:
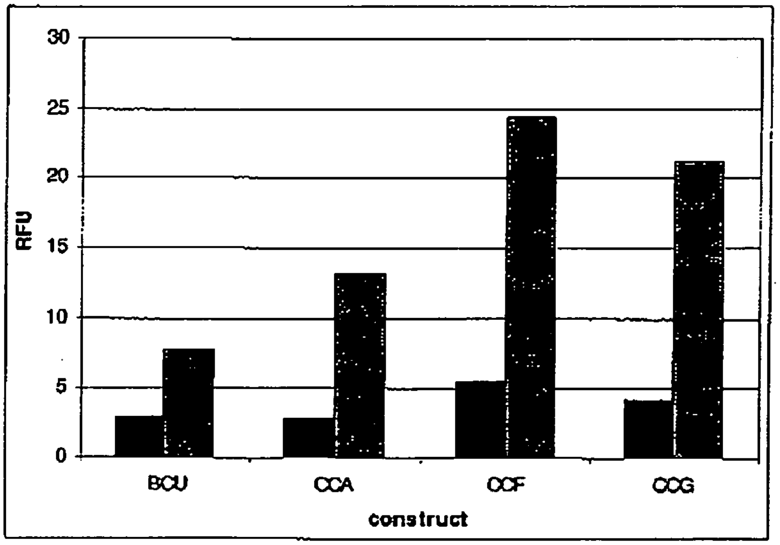

HBG was constructed using the extended globulin-1 promoter of U.S. Pat. No. 7,169,967, incorporated herein by reference, and seen in FIG. 3, SEQ ID NO: 6, with sequence modification as described for SEQ ID NO: 11. See FIG. 7 for the plasmid map. Two plant transcription units (PTUs), each consisting of a promoter, protein coding sequence, and termination sequence, were placed one next to the other such that 191 bp of sequence separated the end of the first PTU's termination sequence and the beginning of the next PTU's promoter sequence. This was achieved by cutting the HBF vector in two separate reactions. The first reaction cut with PmeI to linearize the vector. The second reaction cut with PmeI and NheI and the NheI 5' overhang was filled in using a Klenow fragment. This second fragment consisted of spacer DNA sequence, the extended globulin promoter, the HBsAg coding sequence, and the PinII termination sequence. The PmeI/filled NheI fragment was inserted into the linearized vector's PmeI site using a blunt end ligation and the orientation of the fragment was screened using restriction fragment analysis. This resulted in a two PTU vector.

Figure 8:
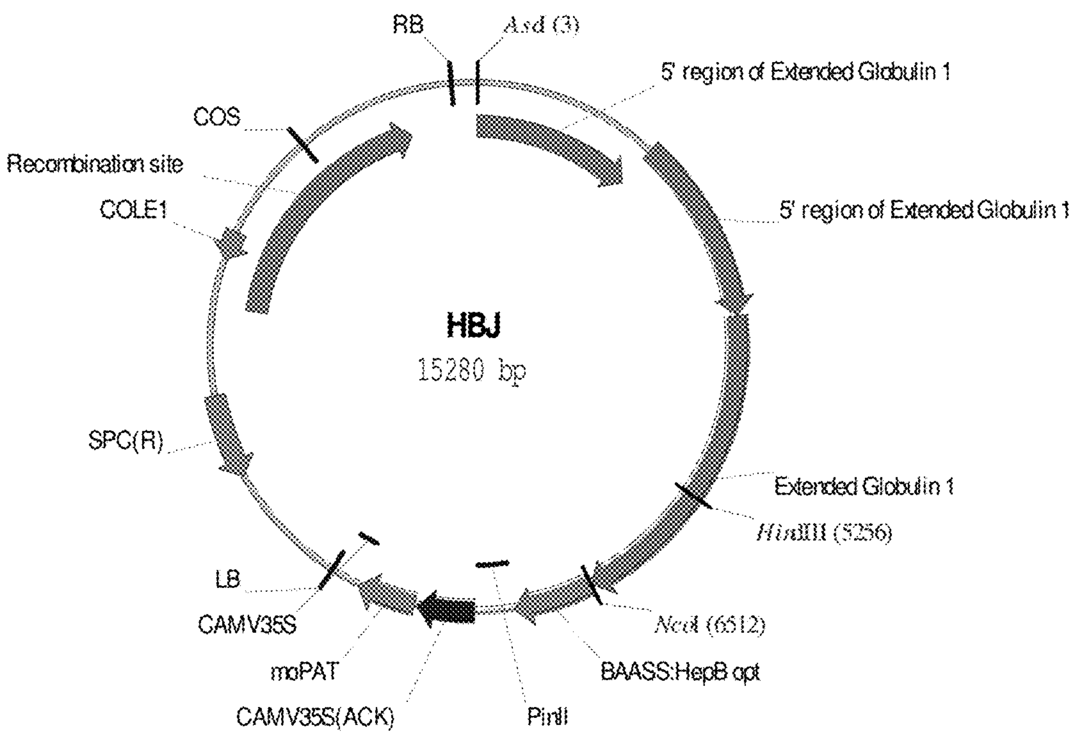
FIG. 8 is a map of plasmid HBJ used in the experiments below.

HBJ used the enhanced globulin-1 promoter described in Example 2. The first 1745 bp of the promoter sequence in HBF were amplified using PCR. The forward primer incorporated the existing AscI site at the 5' end of the promoter, and the reverse primer replaced the HindIII restriction site with a MluI site. The 5' promoter PCR fragment was cloned into a pGEMTeasy vector and then inserted into the AscI site of the HBF vector. The orientation of the fragment was screened by restriction digest so that the AscI site was maintained at the 5' end of the promoter, and the MluI/AscI junction abolished both enzyme restriction sites at the 3' end of the fragment. This produced a 2× enhanced globulin promoter. The previous step was repeated to yield the 3× enhanced globulin promoter. The plasmid map is shown in FIG. 8.

PMY and PMZ Constructs:

In order to confirm the 3× enhanced globulin-1 promoter could increase expression of proteins other than HBsAg, constructs were created with the 2× and 3× enhanced globulin-1 promoter driving GUS (PMY and PMZ, respectively). The GUS sequence is shown in FIG. 1A (SEQ ID NO: 1) To produce these constructs, the vector containing the 2× extended globulin promoter driving HBsAg expression was cut by NcoI and Pad so that the HBsAg and BAASS cell wall targeting sequence could be replaced by an NcoI and Pad restriction digested GUS sequence. This produced the PMY construct.

Figure 9:
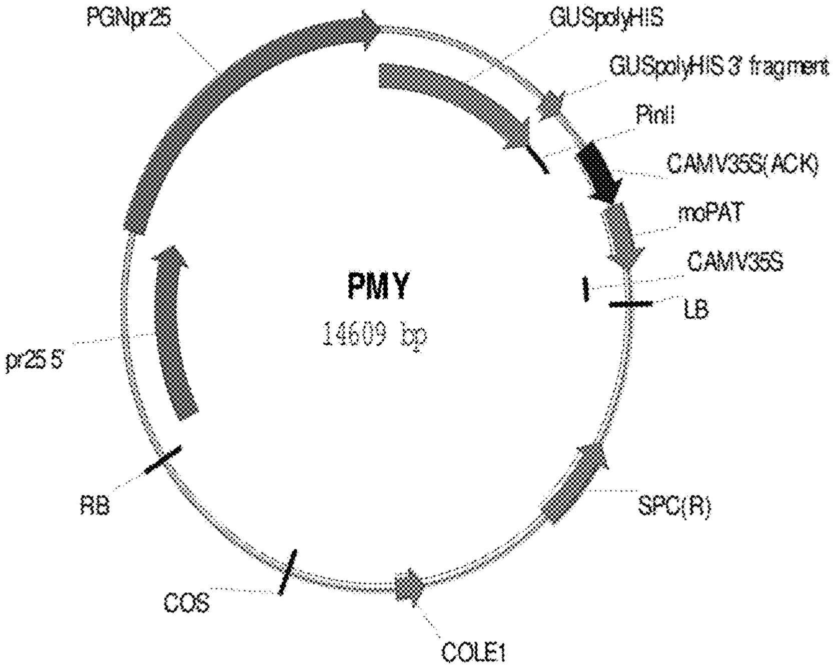
FIG. 9 is a map of plasmid PMY used in the experiments below.
Figure 10:
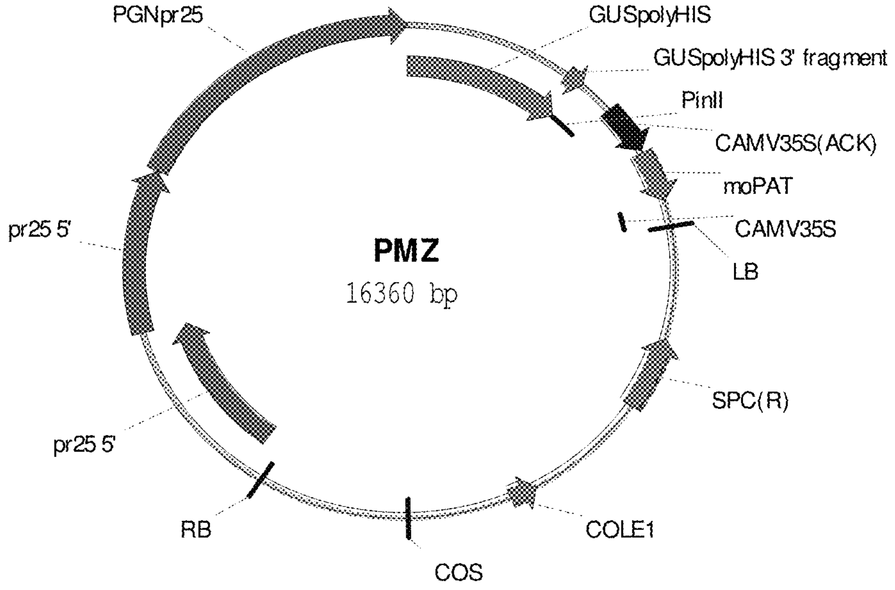
FIG. 10 is a map of plasmid PMZ used in the experiments below.

A parallel strategy was used for the PMZ construct (replaced HBsAg and cell wall sequence in HBJ with GUS). See FIGS. 9 and 10 for plasmid maps of the PMY and PMZ constructs.

Transformation

HBA, HBE, HBF, HBG, HBJ, PMY, and PMZ constructs were all transformed into maize plants using an *Agrobacterium tumefaciens* superbinary vector transformation system. *Zea mays* was used as the host plant and regeneration of plants were conducted in growth chambers and greenhouses to generate $T_0$ plants producing $T_1$ seed. Expression levels for HBA, HBE, HBF, HBG, and HBJ $T_1$ seed were assayed using a sandwich ELISA Protocol as Briefly Described below:

Extraction of HBsAg from seed: 100 mg of ground seed samples were agitated in 1 mL of extraction buffer (PBS with 1% Triton X-100), centrifuged, and supernatant diluted and applied to the ELISA plate.

Assay for HBsAg on 96-well plate: Rabbit anti-HBsAg antibody was used to coat 96-well plates, corn extracts were added to the coated plates, followed by biotinylated rabbit anti-HBsAg, streptavidin conjugated to alkaline phosphatase, and finally pNPP substrate. Washes were conducted between each step using $PBST_{0.05\%}$, and blocking solution was 3% BSA in PBST.

Results

Below is a summary table showing the top 10% expressing lines for the various constructs.

(Note: % TSP=% total soluble protein (ug of HepB/100 ug of total soluble protein)

TABLE 1

| Construct | % TSP |
|---|---|
| HBE | 0.12 |
| HBF | 0.40 |
| HBG | 0.41 |
| HBJ | 0.51 |

Figure 11:
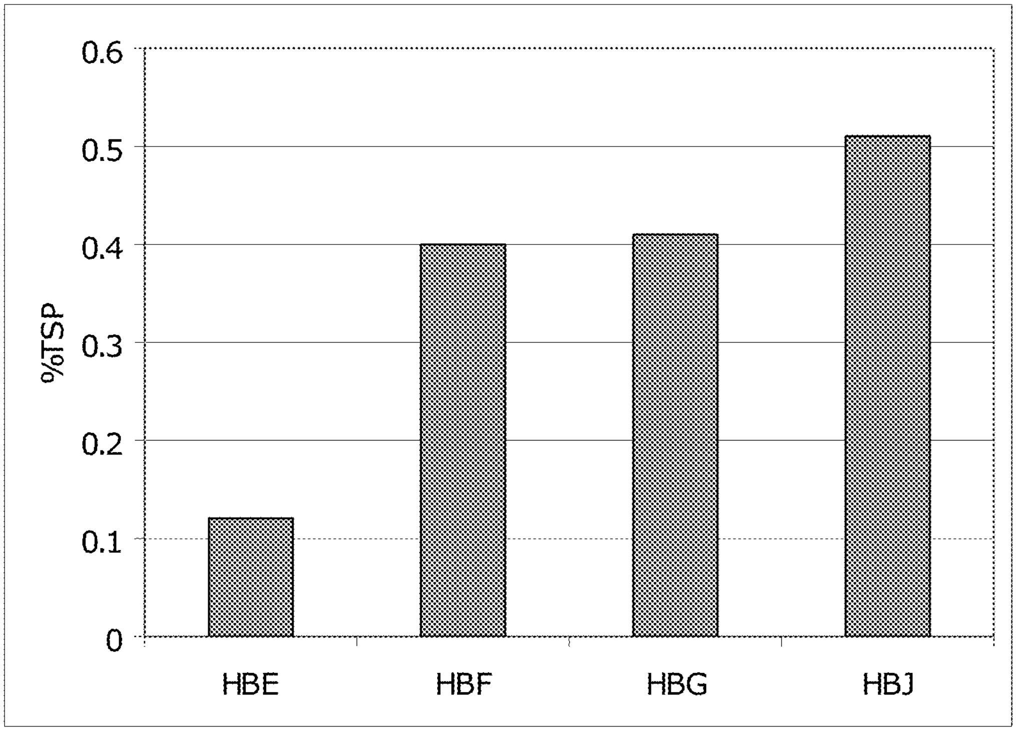
FIG. 11 is a graph summarizing results of expression levels achieved in total soluble protein using the constructs described.

See FIG. 11 for a graph showing expression levels. As can be seen, the enhanced globulin-1 promoter provided increased expression compared to constructs using a single copy or two copies of the promoter.

PMY and PMZ $T_1$ seed were produced and will be assayed for GUS activity using an ELISA protocol.

REFERENCES

Altschul, S. F., Gish, W., Miller, W., Myers, E. W. and Lipman, D. J. (1990) Basic local alignment search tool. J. Mol. Biol. 215, 403-410.

Altschul, S. F., Madden, T. L., Schaffer, A. A., Zhang, J., Zhang, Z., Miller, W. and Lipman, D. J. (1997) Nucleic Acids Res. 25, 3389-3402.

An, G., Mitra, A., Choi, H. K., Costa, M. A., An, K., Thornburg, R. W. and Ryan, C. A. (1989) Functional analysis of the 3' control region of the potato wound-inducible proteinase inhibitor II gene. Plant Cell 1, 115-122.

Anderson, E. (1944) Sources of effective germplasm in hybrid maize. Annals of the Missouri Botanical Garden 31, 355-361.

Armstrong, C. I. and Green, C. E. (1985) Establishment and maintenance of friable, embryogenic maize callus and involvement of L-proline. Planta 154, 207-214.

Armstrong, C., Green, C. and Phillips, R. (1991) Development and availability of germplasm with high type II culture response. Maize Genet. Coop. News Lett. 65, 92-93.

Ausubel F. M., Brent, R., Kingston, R. E., Moore, D. D., Seidman, J. G., Smith, J. A. and Struhl, K. (Eds.) (1993) Current Protocols in Molecular Biology, John Wiley & Sons, New York.

Bailey, M. R., Woodard, S. L., Callaway, E., Beifuss, K., Magallanes-Lundback, M., Lane, J. R., Horn, M. E., Mallubhotla, H., Delaney, D. D., Ward, M., Van Gastel, F., Howard, J. A. and Hood, E. E. (2004) Improved recovery of active recombinant laccase from maize seed. Appl. Microbiol. Biotechnol. 63, 390-397.

Becker, T. W., Templeman, T. S., Viret, J. F. and Bogorad, L. (1992) The cab-m7 gene: a light-inducible, mesophyll-specific gene of maize. Plant Mol. Biol. 20, 49-60.

Belanger, F. C. and Kriz, A. L. (1991) Molecular basis for allelic polymorphism of the maize globulin-1 gene. Genetics 129, 863-872.

Bradford, M. M. (1976) A rapid and sensitive method for the quantitation of microgram quantities of protein utilizing the principle of protein-dye binding. Anal. Biochem. 72, 248-254.

Brinch-Pedersen, H., Hatzack, F., Sørensen, L. D. and Holm, P. B. (2003) Concerted action of endogenous and heterologous phytase on phytic acid degradation in seed of transgenic wheat (*Triticum aestivum* L.). Transgenic Res. 12, 649-659.

Broglie, R., Coruzzi, G., Fraley, R. T., Rogers, S. G., Horsch, R. B., Niedermeyer, J. G., Fink, C. L. and Chua, N. H. (1984) Light-regulated expression of a pea ribulose-1,5-bisphosphate carboxylase small subunit gene in transformed plant cells. Science 224, 838-843.

Bustos, M. M., Guiltinan, M. J., Jordano, J., Begum, D., Kalkan, F. A. and Hall, T. C. (1989) Regulation of beta-glucuronidase expression in transgenic tobacco plants by an A/T-rich, cis-acting sequence found upstream of a French bean beta-phaseolin gene. Plant Cell 1, 839-853.

Caddick M. X., Greenland, A. J., Jepson, I., Krause, K. P., Qu, N., Riddell, K. V., Salter, M. G., Schuch, W., Sonnewald, U. and Tomsett, A. B. (1998) An ethanol inducible gene switch for plants used to manipulate carbon metabolism. Nat. Biotechnol. 16, 177-180.

Carrillo, C., Wigdorovitz, A., Oliveros, J. C., Zamorano, P. I., Sadir, A. M., Gomez, N., Salinas, J., Escribano, J. M. and Borca, M. V. (1998) Protective immune response to foot-and-mouth disease virus with VP1 expressed in transgenic plants. J. Virol. 72, 1688-1690.

Casas, A. M., Kononowicz, A. K., Zehr, U. B., Tomes, D. T., Axtell, J. D., Butler, L. G., Bressan, R. A. and Hasegawa P. M. (1993) Transgenic sorghum plants via microprojectile bombardment. Proc. Natl. Acad. Sci. USA 90, 11212-11216.

Chatterjee, M., Sparvoli, S., Edmunds, C., Garosi, P., Findlay, K. and Martin, C. (1996) DAG, a gene required for chloroplast differentiation and palisade development in Antirrhinum majus. EMBO J. 15, 4194-4207.

Christensen, A. H., Sharrock, R. A. and Quail, P. H. (1992) Maize polyubiquitin genes: structure, thermal perturbation of expression and transcript splicing, and promoter activity following transfer to protoplasts by electroporation. Plant Mol. Biol. 18, 675-689.

Cornejo, M. J., Luth, D., Blankenship, K. M., Anderson, O. D. and Blechl, A. E. (1993) Activity of a maize ubiquitin promoter in transgenic rice. Plant Mol. Biol. 23, 567-581.

Corpet, F. (1988) Multiple sequence alignment with hierarchical clustering. Nucleic Acids Res. 16, 10881-10890.

Coruzzi, G., Broglie, R., Edwards, C. and Chua, N. H. (1984) Tissue-specific and light-regulated expression of a pea nuclear gene encoding the small subunit of ribulose-1,5-bisphosphate carboxylase. EMBO J. 3, 1671-1679.

Creissen, G., Edwards, E. A., Enard, C., Wellburn, A. and Mullineaux, P. (1992) Molecular characterization of glutathione reductase cDNA from pea (*Pisum sativum* L.). Plant J. 2, 129-131.

Crossway, A. (1985) Mol. Gen. Genet. 202, 179-185.

Daniell, H., Streatfield, S. J. and Wycoff, K. (2001) Medical molecular farming: production of antibodies, biopharmaceuticals and edible vaccines in plants. Trends Plant Sci. 6, 219-226.

De Wilde, C., Van Houdt, H., De Buck, S., Angenon, G., De Jaeger, G. and Depicker, A. (2000) Plants as bioreactors for protein production: avoiding the problem of transgene silencing. Plant Mol. Biol. 43, 347-359.

Della-Cioppa et al. (1987) Plant Physiology 84:965-968

Elroy-Stein et al. (1989) PNAS USA 86:6126-6130)

Estruch, J. J., Carozzi, N. B., Desai, N., Duck, N. B., Warren, G. W. and Koziel, M. G. (1997) Transgenic plants: an emerging approach to pest control. Nat. Biotechnol. 15, 137-141.

Feinberg, A. P. and Vogelstein, B. (1983) A technique for radiolabeling DNA restriction endonuclease fragments to high specific activity. Anal. Biochem. 132, 6-13.

Fontes, E. B., Shank, B. B., Wrobel, R. L., Moose, S. P., OBrian, G. R., Wurtzel, E. T. and Boston, R. S. (1991) Characterization of an immunoglobulin binding protein homolog in the maize floury-2 endosperm mutant. Plant Cell 3, 483-496.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L. and Woo, S. C. (1983) Expression of bacterial genes in plant cells. Proc. Natl. Acad. Sci. USA, 80, 4803-4807.

Fromm, M., Taylor, L. P. and Walbot, V. (1985) Expression of genes transferred into monocot and dicot plant cells by electroporation. Proc. Natl. Acad. Sci. USA 82, 5824-5828.

Fromm, M. E., Morrish, F., Armstrong, C., Williams, R., Thomas, J. and Klein, T. M. (1990) Inheritance and expression of chimeric genes in the progeny of transgenic maize plants. Biotechnology (N Y) 8, 833-839.

Gallie. (1989) Molecular Biology of RNA, ed. Cech (Liss, N.Y.

Gallie et al. (1995) Gene 165(2):233-238

Geffers, R., Cerff, R. and Hehl, R. (2000) Anaerobiosis-specific interaction of tobacco nuclear factors with cis-regulatory sequences in the maize GapC4 promoter. Plant Mol. Biol. 43, 11-21.

Gordon-Kamm, W., Dilkes, B. P., Lowe, K., Hoerster, G., Sun, X., Ross, M., Church, L., Bunde, C., Farrell, J., Hill, P., Maddock, S., Snyder, J., Sykes, L., Li, Z., Woo, Y. M., Bidney, D. and Larkins, B. A. (1990) Transformation of maize cells and regeneration of fertile transgenic plants. Plant Cell 2, 603-618.

Gould, S. J., Keller, G. A., Hosken, N., Wilkinson, J. and Subramani, S. (1989) A conserved tripeptide sorts proteins to peroxisomes. J. Cell. Biol. 108, 1657-1664.

Grdzelishvili, V. Z., Chapman, S. N., Dawson, W. O. and Lewandowski, D. J. (2000) Mapping of the tobacco mosaic virus movement protein and coat protein subgenomic RNA promoters in vivo. Virology 275, 177-192.

Gruber et al. (1993) Vectors for plant transformation. In: Glick, B. R. and Thompson J. E. (Eds.) Methods in Plant Molecular Biology and Biotechnology, CRC Press, pp. 89-119.

Guilley, H., Dudley, R. K., Jonard, G., Balazs, E. and Richards, K. E. (1982) Transcription of Cauliflower mosaic virus DNA: detection of promoter sequences, and characterization of transcripts. Cell 30, 763-773.

Gurley, W. B., Czarnecka, E., Nagao, R. T. and Key, J. L. (1986) Upstream sequences required for efficient expression of a soybean heat shock gene. Mol. Cell. Biol. 6, 559-565.

Haq, T. A., Mason, H. S., Clements, J. D. and Arntzen, C. J. (1995) Oral immunization with a recombinant bacterial antigen produced in transgenic plants. Science 268, 714-716.

Hiei, Y., Ohta, S., Komari, T. and Kumashiro, T. (1994) Efficient transformation of rice (*Oryza sativs* L.) mediated by *Agrobacterium* and sequence analysis of the boundaries of the T-DNA. Plant J. 6, 271-282.

Higgins, D. G. and Sharp, P. M. (1988) CLUSTAL: a package for performing multiple sequence alignment on a microcomputer. Gene 73, 237-244.

Higgins, D. G. and Sharp, P. M. (1989) Fast and sensitive multiple sequence alignments on a microcomputer. Comput. Appl. Biosci. 5, 151-153.

Hood, E. E., Helmer, G. L., Fraley, R. T. and Chilton, M. D. (1986) The hypervirulence of *Agrobacterium tumefaciens* A281 is encoded in a region of pTiBo542 outside of T-DNA. J. Bacteriol. 168, 1291-1301.

Hood, E. E., Witcher, D. R., Maddock, S., Meyer, T., Baszczynski, C., Bailey, M., Flynn, P., Register, J., Marshall, L., Bond, D., Kulisek, E., Kusnadi, A., Evangelista, R., Nikolov, Z., Wooge, C., Mehigh, R. J., Hernan, R., Kappel, W. K., Ritland, D., Li, C-P. and Howard, J. A. (1997) Commercial production of avidin from transgenic maize: characterization of transformant, production, processing, extraction and purification. Mol. Breed. 3, 291-306.

Hood, E. E., Woodard, S. L. and Horn, M. E. (2002) Monoclonal antibody manufacturing in transgenic plants—myths and realities. Curr. Opin. Biotechnol. 13, 630-635.

Hood, E. E., Bailey, M. R., Beifuss, K., Magallanes-Lundback, M., Horn, M. E., Callaway, E., Drees, C., Delaney, D. E., Clough, R. and Howard, J. A. (2003) Criteria for high-level expression of a fungal laccase gene in transgenic maize. Plant Biotechnol. J. 1, 129-140.

Huang, X., Miller, W., Schwartz, S, and Hardison, R. C. (1992) Parallelization of a local similarity algorithm. Comput. Appl. Biosci. 8, 155-65.

Innis, M., Gelfand, D., Sninsky, J. and White, T. (1990) PCR Protocols: A Guide to Methods and Applications. Academic Press, New York.

Innis, M., Gelfand, D. and Sninsky, J. (1995) PCR Strategies. Academic Press, New York.

Innis, M., Gelfand, D. and Sninsky, J. (1999) PCR Applications: Protocols for Functional Genomics. Academic Press, New York.

Ishida, Y., Saito, H., Ohta, S., Hiei, Y., Komari, T. and Kumashiro, T. (1996) High efficiency transformation of maize (*Zea mays* L.) mediated by *Agrobacterium tumefaciens*. Nat. Biotechnol. 14, 745-750.

Jefferson, R. A., Kavanagh, T. A. and Bevan, M. W. (1987) GUS fusions: beta-glucuronidase as a sensitive and versatile gene fusion marker in higher plants. EMBO J. 6, 3901-7.

Jensen, N. F. (1988) Plant Breeding Methodology. Interscience.

Jobling et al. (1987) Nature 325:622-625

Kalderon, D., Roberts, B. L., Richardson, W. D. and Smith A. E. (1984) A short amino acid sequence able to specify nuclear location. Cell 39, 499-509.

Karlin, S, and Altschul, S. F. (1990) Methods for assessing the statistical significance of molecular sequence features by using general scoring schemes. Proc. Natl. Acad. Sci. USA 87, 2264-2268.

Karlin, S, and Altschul, S. F. (1993) Applications and statistics for multiple high-scoring segments in molecular sequences. Proc. Natl. Acad. Sci. USA 90, 5873-5877.

Klein, T. M., Arentzen, R., Lewis, P. A. and Fitzpatrick-McElligott, S. (1992) Transformation of microbes, plants and animals by particle bombardment. Biotechnology (N Y) 10, 286-291.

Lamphear, B. J., Streatfield, S. J., Jilka, J. M., Brooks, C. A., Barker, D. K., Turner, D. D., Delaney, D. E., Garcia, M., Wiggins, W., Woodard, S. L., Hood, E. E., Tizard, I. R., Lawhorn, B. and Howard, J. A. (2002) Delivery of subunit vaccines in maize seed. J. Control. Release 85, 169-180.

Lee, N., Wang, Y., Yang, J., Ge, K., Huang, S., Tan, J. and Testa, D. (1991) Efficient transformation and regeneration of rice small cell groups. Proc. Nat. Acad. Sci. USA 88, 6389-6393.

Lessard, P. A., Kulaveerasingam, H., York, G. M., Strong, A. and Sinskey, A. J. (2002) Manipulating gene expression for the metabolic engineering of plants. Metab. Eng. 4, 67-79.

Leung, J., Fukuda, H., Wing, D., Schell, J. and Masterson, R. (1991) Functional analysis of cis-elements, auxin response and early developmental profiles of the mannopine synthase bi-directional promoter. Mol. Gen. Genet. 230, 463-474.

Lommel et al. (1991) Virology 81:382-385

Macejak et al. (1991) Nature 353:90-94

Maiti, I. B., Gowda, S., Kiernan, J., Ghosh, S. K. and Shepherd, R. J. (1997) Promoter/leader deletion analysis and plant expression vectors with the figwort mosaic virus (FMV) full length transcript (FLt) promoter containing single or double enhancer domains. Transgenic Res. 6, 143-156.

Mason, H. S., Lam, D. M. and Arntzen, C. J. (1992) Expression of hepatitis B surface antigen in transgenic plants. Proc. Natl. Acad. Sci. USA 89, 11745-11749.

Mathur, J. and Koncz, C. (1998) PEG-mediated protoplast transformation with naked DNA. Methods Mol. Biol. 82, 267-276.

Matsuoka, K. and Nakamura, K. (1991) Propeptide of a precursor to a plant vacuolar protein required for vacuolar targeting. Proc. Natl. Acad. Sci. USA 88, 834-838.

Meinkoth, J. and Wahl, G. (1984) Hybridization of nucleic acids immobilized on solid supports. Anal. Biochem. 138, 267-284.

Miki, B. and McHugh, S. (2004) Selectable marker genes in transgenic plants: applications, alternatives and biosafety. J. Biotechnol. 107, 193-232.

Moloney, M. et al. (1989) High efficiency transformation of *Brassica napus* using *Agrobacterium* vectors. Plant Cell Reports 8, 238-242.

Myers, E. W. and Miller, W. (1988) Optimal alignments in linear space. Comput. Appl. Biosci. 4, 11-17.

Needleman, S. B. and Wunsch, C. D. (1970) A general method applicable to the search for similarities in the amino acid sequence of two proteins. J. Mol. Biol. 48, 443-453.

Nessler, C. L. (1994) Metabolic engineering of plant secondary products. Transgenic Res. 3, 109-115.

Neuhausen, S. (1989) A survey of Iowa Stiff Stalk parents derived inbreds and BSSS(HT)C5 using RFLP analysis. MNL 63, 110-111.

Odell, J. T., Nagy, F. and Chua, N. H. (1985) Identification of DNA sequences required for activity of the cauliflower mosaic virus $^{35}$S promoter. Nature 313, 810-812.

Oldach, K. H., Becker, D. and Lorz, H. (2001) Heterologous expression of genes mediating enhanced fungal resistance in transgenic wheat. Mol. Plant. Microbe Interact. 14, 832-838.

Pearson, W. R. and Lipman, D. J. (1988) Improved tools for biological sequence comparison. Proc. Natl. Acad. Sci. USA 85, 2444-2448.

Pearson, W. R. (1994) Using the FASTA program to search protein and DNA sequence databases. Methods Mol. Biol. 24, 307-331.

Poehlman, J. M. and Sleper, D. A. (1995) Breeding field crops, 4$^{th}$ Edition, Iowa State University Press.

Poirier, Y., Nawrath, C. and Somerville, C. (1995) Production of polyhydroxyalkanoates, a family of biodegradable plastics and elastomers, in bacteria and plants. Biotechnology (N Y) 13, 142-150.

Rogers, J. C. (1985) Two barley alpha-amylase gene families are regulated differently in aleurone cells. J. Biol. Chem. 260, 3731-3738.

Roussell, D. L., Boston, R. S., Goldsbrough, P. B. and Larkins, B. A. (1988) Deletion of DNA sequences flanking an Mr 19,000 zein gene reduces its transcriptional activity in heterologous plant tissues. Mol. Gen. Genet. 211, 202-209.

Russell, D. A. and Fromm, M. E. (1997) Tissue-specific expression in transgenic maize of four endosperm promoters from maize and rice. Transgenic Res. 6, 157-168.

Sambrook, J., Fritsch, E. F. and Maniatis, T. (1989) Molecular Cloning: A Laboratory Manual, 2$^{nd}$ Edition. Cold Spring Harbor Laboratory Press, Plainview, N.Y.

Smith, T. F. and Waterman, M. S. (1981) Adv. Appl. Math. 2, 482-489.

Stacey, J. and Issac, P. G. (1994) Isolation of DNA from plants. Methods Mol. Biol. 28, 9-15.

Sprague, G. F. (1946) Early testing of inbred lines of maize. J. Amer. Soc. Agron. 38, 108-117.

Stiefel, V., Ruiz-Avila, L., Raz, R., Pilar Valles, M., Gomez, J., Pages, M., Martinez-Izquierdo, J. A., Ludevid, M. D., Langdale, J. A., Nelson, T., et al. (1990) Expression of a maize cell wall hydroxyproline-rich glycoprotein gene in early leaf and root vascular differentiation. Plant Cell 2, 785-793.

Streatfield, S. J., Jilka, J. M., Hood, E. E., Turner, D. D., Bailey, M. R., Mayor, J. M., Woodard, S. L., Beifuss, K., Horn, M. E., Delaney, D. E., Tizard, I. R. and Howard, J. A. (2001) Plant-based vaccines: unique advantages. Vaccine 19, 2742-2748.

Streatfield, S. J., Mayor, J. M., Barker, D. K., Brooks, C., Lamphear, B. J., Woodard, S. L., Beifuss, K. K., Vicuna, D. V., Massey, L. A. Massey, Horn, M. E., Delaney, D. D., Nikolov, Z. L., Hood, E. E., Jilka, J. M. and Howard, J. A. (2002) Development of an edible subunit vaccine in corn against enterotoxigenic strains of *Escherichia coli*. In Vitro Cell. Dev. Biol.-Plant 38, 11-17.

Streatfield, S. J., Lane, J. R., Brooks, C. A., Barker, D. K., Poage, M. L., Mayor, J. M., Lamphear, B. J., Drees, C. F., Jilka, J. M., Hood, E. E. and Howard, J. A. (2003) Corn as a production system for human and animal vaccines. Vaccine 21, 812-815.

Takimoto, I., Christensen, A. H., Quail, P. H., Uchimiya, H. and Toki, S. (1994) Non-systemic expression of a stress-response maize polyubiquitin gene (Ubi-1) in transgenic rice plants. Plant Mol. Biol. 26, 1007-1012.

Velten, J. and Schell, J. (1985) Selection-expression plasmid vectors for use in genetic transformation of higher plants. Nucleic Acids Res. 13, 6981-6998.

Vilardell, J., Mundy, J., Stilling, B., Leroux, B., Pla, M., Freyssinet, G. and Pages, M. (1991) Regulation of the maize rab 17 gene promoter in transgenic heterologous systems. Plant Mol. Biol. 17, 985-993.

Wan, Y. and Lemaux, P. G. (1994) Generation of large numbers of independently transformed fertile barley plants. Plant Physiol. 104, 37-48.

Waterhouse, P. M., Wang, M. B. and Lough, T. (2001) Gene silencing as an adaptive defense against viruses. Nature 411, 834-842.

Weigel, D. and Nilsson, O. (1995) A developmental switch sufficient for flower initiation in diverse plants. Nature 377, 495-500.

Weising, K., Schell, J. and Kahl, G. (1988) Foreign genes in plants: transfer, structure, expression, and applications. Annu. Rev. Genet. 22, 421-477.

Wohlleben, W., Arnold, W., Broer, I., Hillemann, D., Strauch, E. and Puhler, A. (1988) Nucleotide sequence of the phosphinothricin N-acetyltransferase gene from *Streptomyces virochromogenes* Tu494 and its expression in *Nicotiana tabacum*. Gene 70, 25-37.

Woodard, S. L., Mayor, J. M., Bailey, M. R., Barker, D. K., Love, R. T., Lane, J. R., Delaney, D. E., McComas-Wagner, J. M., Mallubhotla, H. D., Hood, E. E., Dangott, L. J., Tichy, S. E. and Howard, J. A. (2003) Maize-derived bovine trypsin: characterization of the first large-scale, commercial protein product from transgenic plants. Biotechnol. Appl. Biochem. 38, 123-130.

Yang, N. S. and Russell, D. (1990) Maize sucrose synthase-1 promoter drives phloem cell-specific expression of GUS gene in transgenic tobacco plants. Proc. Natl. Acad. Sci. USA 87, 4144-4148.

Ye, X., Al-Babili, S., Kloti, A., Zhang, J., Lucca, P., Beyer, P. and Potrykus, I. (2000) Engineering the provitamin A (beta-carotene) biosynthetic pathway into (carotenoid-free) rice endosperm. Science 287, 303-305.

Yu, H. and Kumar, P. P. (2003) Post-transcriptional gene silencing in plants by RNA. Plant Cell Rep. 22, 167-174.

Zhong, G-Y, Peterson, D., Delaney, D. E., Bailey, M., Witcher, D. R., Register, J. C. (III), Bond, D., Li, C-P., Marshall, L., Kulisek, E., Ritland, D., Meyer, T., Hood, E. E. and Howard, J. A. (1999) Commercial production of aprotinin in transgenic maize seeds. Mol. Breed. 5, 345-356.

What is claimed is:

1. A DNA construct comprising an enhanced globulin-1 regulatory region comprising three copies of SEQ ID NO: 10 operably linked to a nucleic acid molecule.

2. A vector comprising the DNA construct of claim 1.

3. A plant, plant part or plant cell comprising the DNA construct of claim 1.

4. A method of increasing expression of a nucleic acid molecule in a plant, plant part or plant cell, the method comprising introducing into said plant, plant part or cell a DNA construct, said DNA construct comprising an enhanced globulin-1 regulatory region operably linked to a nucleic acid molecule, said enhanced globulin-1 regulatory region comprising three copies of SEQ ID NO: 10, wherein said nucleic acid molecule is expressed at a higher level in a plant, plant part, or plant cell as compared to the expression of two copies of said nucleic acid molecule each copy operably linked to one copy of SEQ ID NO: 10.

5. The method of claim 4, said method further comprising assaying said plant, plant part or plant cell for expression of said operably linked nucleic acid molecule and selecting the plants, plant parts or plant cells having said higher level of expression.

* * * * *

SEQUENCE LISTING

<160> NUMBER OF SEQ ID NOS: 31

<210> SEQ ID NO 1
<211> LENGTH: 1824
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
atggtccgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat ttgaagccga tgtcacgccg     360
tatgttattg ccgggaaaag tgtacgtatc accgtttgtg tgaacaacga actgaactgg     420
cagactatcc cgccgggaat ggtgattacc gacgaaaacg gcaagaaaaa gcagtcttac     480
ttccatgatt tctttaacta tgccggaatc catcgcagcg taatgctcta caccacgccg     540
aacacctggg tggacgatat caccgtggtg acgcatgtcg cgcaagactg taaccacgcg     600
```

-continued

```
tctgttgact gccaggtggt ggccaatggt gatgtcagcg ttgaactgcg tgatgcggat    660

caacaggtgg ttgcaactgg acaaggcact agcgggactt tgcaagtggt gaatccgcac    720

ctctgccaac cgggtgaagg ttatctctat gaactgtgcg tcacagccaa aagccagaca    780

gagtgtgata tctacccgct tcgcgtcggc atccggtcag tggcagtgaa gggccaacag    840

ttcctgatta accacaaacc gttctacttt actggctttg gtcgtcatga agatgcggac    900

ttacgtggca aaggattcga taacgtgctg atggtgcacg accacgcatt aatggactgg    960

attggggcca actcctaccg tacctcgcat tacccttacg ctgaagagat gctcgactgg   1020

gcagatgaac atggcatcgt ggtgattgat gaaactgctg ctgtcggctt taacctctct   1080

ttaggcattg gtttcgaagc gggcaacaag ccgaaagaac tgtacagcga agaggcagtc   1140

aacggggaaa ctcagcaagc gcacttacag gcgattaaag agctgatagc gcgtgacaaa   1200

aaccacccaa gcgtggtgat gtggagtatt gccaacgaac cggatacccg tccgcaagtg   1260

cacgggaata tttcgccact ggcggaagca acgcgtaaac tcgacccgac gcgtccgatc   1320

acctgcgtca atgtaatgtt ctgcgacgct cacaccgata ccatcagcga tctctttgat   1380

gtgctgtgcc tgaaccgtta ttacggatgg tatgtccaaa gcggcgattt ggaaacggca   1440

gagaaggtac tggaaaaaga acttctggcc tggcaggaga aactgcatca gccgattatc   1500

atcaccgaat acggcgtgga tacgttagcc gggctgcact caatgtacac cgacatgtgg   1560

agtgaagagt atcagtgtgc atggctggat atgtatcacc gcgtctttga tcgcgtcagc   1620

gccgtcgtcg gtgaacaggt atggaatttc gccgattttg cgacctcgca aggcatattg   1680

cgcgttggcg gtaacaagaa agggatcttc actcgcgacc gcaaaccgaa gtcggcggct   1740

tttctgctgc aaaaacgctg gactggcatg aacttcggtg aaaaaccgca gcagggaggc   1800

aaacaacacc atcaccatca ccat                                          1824
```

```
<210> SEQ ID NO 2
<211> LENGTH: 608
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Val Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140
```

-continued

```
Pro Gly Met Val Ile Thr Asp Glu Asn Gly Lys Lys Lys Gln Ser Tyr
145                 150                 155                 160

Phe His Asp Phe Phe Asn Tyr Ala Gly Ile His Arg Ser Val Met Leu
                165                 170                 175

Tyr Thr Thr Pro Asn Thr Trp Val Asp Asp Ile Thr Val Val Thr His
            180                 185                 190

Val Ala Gln Asp Cys Asn His Ala Ser Val Asp Cys Gln Val Val Ala
        195                 200                 205

Asn Gly Asp Val Ser Val Glu Leu Arg Asp Ala Asp Gln Gln Val Val
    210                 215                 220

Ala Thr Gly Gln Gly Thr Ser Gly Thr Leu Gln Val Val Asn Pro His
225                 230                 235                 240

Leu Cys Gln Pro Gly Glu Gly Tyr Leu Tyr Glu Leu Cys Val Thr Ala
                245                 250                 255

Lys Ser Gln Thr Glu Cys Asp Ile Tyr Pro Leu Arg Val Gly Ile Arg
            260                 265                 270

Ser Val Ala Val Lys Gly Gln Gln Phe Leu Ile Asn His Lys Pro Phe
        275                 280                 285

Tyr Phe Thr Gly Phe Gly Arg His Glu Asp Ala Asp Leu Arg Gly Lys
    290                 295                 300

Gly Phe Asp Asn Val Leu Met Val His Asp His Ala Leu Met Asp Trp
305                 310                 315                 320

Ile Gly Ala Asn Ser Tyr Arg Thr Ser His Tyr Pro Tyr Ala Glu Glu
                325                 330                 335

Met Leu Asp Trp Ala Asp Glu His Gly Ile Val Val Ile Asp Glu Thr
            340                 345                 350

Ala Ala Val Gly Phe Asn Leu Ser Leu Gly Ile Gly Phe Glu Ala Gly
        355                 360                 365

Asn Lys Pro Lys Glu Leu Tyr Ser Glu Glu Ala Val Asn Gly Glu Thr
    370                 375                 380

Gln Gln Ala His Leu Gln Ala Ile Lys Glu Leu Ile Ala Arg Asp Lys
385                 390                 395                 400

Asn His Pro Ser Val Val Met Trp Ser Ile Ala Asn Glu Pro Asp Thr
                405                 410                 415

Arg Pro Gln Val His Gly Asn Ile Ser Pro Leu Ala Glu Ala Thr Arg
            420                 425                 430

Lys Leu Asp Pro Thr Arg Pro Ile Thr Cys Val Asn Val Met Phe Cys
        435                 440                 445

Asp Ala His Thr Asp Thr Ile Ser Asp Leu Phe Asp Val Leu Cys Leu
    450                 455                 460

Asn Arg Tyr Tyr Gly Trp Tyr Val Gln Ser Gly Asp Leu Glu Thr Ala
465                 470                 475                 480

Glu Lys Val Leu Glu Lys Glu Leu Leu Ala Trp Gln Glu Lys Leu His
                485                 490                 495

Gln Pro Ile Ile Ile Thr Glu Tyr Gly Val Asp Thr Leu Ala Gly Leu
            500                 505                 510

His Ser Met Tyr Thr Asp Met Trp Ser Glu Glu Tyr Gln Cys Ala Trp
        515                 520                 525

Leu Asp Met Tyr His Arg Val Phe Asp Arg Val Ser Ala Val Val Gly
    530                 535                 540

Glu Gln Val Trp Asn Phe Ala Asp Phe Ala Thr Ser Gln Gly Ile Leu
545                 550                 555                 560
```

-continued

```
Arg Val Gly Gly Asn Lys Lys Gly Ile Phe Thr Arg Asp Arg Lys Pro
                565                 570                 575

Lys Ser Ala Ala Phe Leu Leu Gln Lys Arg Trp Thr Gly Met Asn Phe
            580                 585                 590

Gly Glu Lys Pro Gln Gln Gly Gly Lys Gln His His His His His His
        595                 600                 605
```

<210> SEQ ID NO 3
<211> LENGTH: 1401
<212> TYPE: DNA
<213> ORGANISM: Zea mays

<400> SEQUENCE: 3

```
aagcttgccg agtgccatcc ttggacactc gataaagtat attttatttt ttttattttg     60

ccaaccaaac tttttgtggt atgttcctac actatgtaga tctacatgta ccattttggc    120

acaattacat atttacaaaa atgttttcta taaatattag atttagttcg tttatttgaa    180

tttcttcgga aaattcacat ttaaactgca agtcactcga aacatggaaa accgtgcatg    240

caaaataaat gatatgcatg ttatctagca caagttacga ccgatttcag aagcagacca    300

gaatcttcaa gcaccatgct cactaaacat gaccgtgaac ttgttatcta gttgtttaaa    360

aattgtataa aacacaaata aagtcagaaa ttaatgaaac ttgtccacat gtcatgatat    420

catatataga ggttgtgata aaaatttgat aatgtttcgg taaagttgtg acgtactatg    480

tgtagaaacc taagtgacct acacataaaa tcatagagtt tcaatgtagt tcactcgaca    540

aagactttgt caagtgtccg ataaaaagta ctcgacaaag aagccgttgt cgatgtactg    600

ttcgtcgaga tctctttgtc gagtgtcaca ctaggcaaag tctttacgga gtgtttttca    660

ggctttgaca ctcggcaaag cgctcgattc cagtagtgac agtaatttgc atcaaaaata    720

gctgagagat ttaggccccg tttcaatctc acgggataaa gtttagcttc ctgctaaact    780

ttagctatat gaattgaagt gctaaagttt agtttcaatt accaccatta gctctcctgt    840

ttagattaca aatggctaaa agtagctaaa aaatagctgc taaagtttat ctcgcgagat    900

tgaaacaggg ccttaaaatg agtcaactaa tagaccaact aattattagc tattagtcgt    960

tagcttcttt aatctaagct aaaaccaact aatagcttat ttgttgaatt acaattagct   1020

caacggaatt ctctgttttt ctaaaaaaaa actgcccctc tcttacagca aattgtccgc   1080

tgcccgtcgt ccagatacaa tgaacgtacc tagtaggaac tcttttacac gctcggtcgc   1140

tcgccgcgga tcggagtccc cggaacacga caccactgtg gaacacgaca aagtctgctc   1200

agaggcggcc acaccctggc gtgcaccgag ccggagcccg gataagcacg gtaaggagag   1260

tacggcggga cgtggcgacc cgtgtgtctg ctgccacgca gccttcctcc acgtagccgc   1320

gcggccgcgc cacgtaccag ggcccggcgc tggtataaat gcgcgccacc tccgctttag   1380

ttctgcatac agccaaccca a                                               1401
```

<210> SEQ ID NO 4
<211> LENGTH: 1386
<212> TYPE: DNA
<213> ORGANISM: Zea mays

<400> SEQUENCE: 4

```
aagcttgccg agtgccatcc ttggacactc gataaagtat attttatttt ttttattttg     60
ccaaccaaac tttttgtggt atgttcctac actatgtaga tctacatgta ccattttggc    120
acaattacat atttacaaaa atgttttcta taaatattag atttagttcg tttatttgaa    180
```
tttcttcgga aaattcacat ttaaactgca agtcactcga aacatggaaa accgtgcatg 240
caaaataaat gatatgcatg ttatctagca caagttacga ccgatttcag aagcagacca 300
gaatcttcaa gcaccatgct cactaaacat gaccgtgaac ttgttatcta gttgtttaaa 360
aattgtataa aacacaaata aagtcagaaa ttaatgaaac ttgtccacat gtcatgatat 420
catatataga ggttgtgata aaaatttgat aatgtttcgg taaagttgtg acgtactatg 480
tgtagaaacc taagtgacct acacataaaa tcatagagtt tcaatgtagt tcactcgaca 540
aagactttgt caagtgtccg ataaaaagta ctcgacaaag aagccgttgt cgatgtactg 600
ttcgtcgaga tctctttgtc gagtgtcaca ctaggcaaag tctttacgga gtgtttttca 660
ggctttgaca ctcggcaaag cgctcgattc cagtagtgac agtaatttgc atcaaaaata 720
gctgagagat ttaggccccg tttcaatctc acgggataaa gtttagcttc ctgctaaact 780
ttagctatat gaattgaagt gctaaagttt agtttcaatt accaccatta gctctcctgt 840
ttagattaca aatggctaaa agtagctaaa aaatagctgc taaagtttat ctcgcgagat 900
tgaaacaggg ccttaaaatg agtcaactaa tagaccaact aattattagc tattagtcgt 960
tagcttcttt aatctaagct aaaaccaact aatagcttat ttgttgaatt acaattagct 1020
caacggaatt ctctgttttt ctaaaaaaaa actgcccctc tcttacagca aattgtccgc 1080
tgcccgtcgt ccagatacaa tgaacgtacc tagtaggaac tcttttacac gctcggtcgc 1140
tcgccgcgga tcggagtccc cggaacacga caccactgtg gaacacgaca aagtctgctc 1200
agaggcggcc acaccctggc gtgcaccgag ccggagcccg gataagcacg gtaaggagag 1260
tacggcggga cgtggcgacc cgtgtgtctg ctgccacgca gccttcctcc acgtagccgc 1320
gcggccgcgc cacgtaccag ggcccggcgc tggtataaat gcgcgccacc tccgctttag 1380
ttctgc 1386

<210> SEQ ID NO 5
<211> LENGTH: 15
<212> TYPE: DNA
<213> ORGANISM: Zea mays

<400> SEQUENCE: 5
atacagccaa cccaa 15

<210> SEQ ID NO 6
<211> LENGTH: 3006
<212> TYPE: DNA
<213> ORGANISM: Zea mays

<400> SEQUENCE: 6
cggtatgaat ttggaaacaa attcagtact tttaaaaaaa tttgttgtag ggagcaaata 60
atacataaaa taatttatgc attattttat tttttatttg taataatatg cttgaaacga 120
taattcagta tgcatgttgt gccagtgtac tacacgggcg gggggagggg attgagtggg 180
ccagcgcggt gcgtagggta gatgggctga aattgataac tcaagtccga ctaggttctc 240
tttttatttc ccttcctttt ctattttcct ttcttttaat tttcatgctt tcaaactaaa 300
ttcaaattcg agttttgaat ttcagcttct aaattgtaca ctaaaattat atgataaggt 360
aacccctact attactttta attttttat tctaccccat attgtttact taggggagaa 420
taattgactt aatcacattc ttcctaggtt tcaattctca atctttcaaa tccacatttt 480
tagatttcta ttttgaattt aaataccagt ttggatttag agttcaattt caaaatacac 540
aaccaaaata ccagcatgaa tgcaaatata ttttatgttt atgtatttac ttttctttta 600

-continued

```
tactttgctc aaaatagtta ttttcatgta tgaaactcaa taagcaagga actcacgtta    660
ttatataacc taataggaat aatttaggta acataattta tcatcctctt gatttaaaag    720
agatatgcct ccagaataag acacatacta aaaataactc taatattgaa taactaaagt    780
cgtacaaatc tctactatta ttcctataaa ataataaaga actagctaca acttctttaa    840
ggcattattc agggtttaca gcttgagagg catgaaccca tcctgtatac tcctggactt    900
ggaagacaaa atgtcaacca aagtgaaagg ttttcttatg gttgctgcta agagatagat    960
tgaacactag atctctccta agacgtcagg gcatgcgttt agactcctac acatgcgaaa   1020
actgcatctt acagttggaa gaaactatat ctcaccactt cctgcggtgt aactttgccc   1080
aaagatgttg gctcactgtt ggaatcactc cgccccgaac tttggatcta acgcttgcag   1140
tgctacatat tagagcaaga ctaacaatgc cgtggagaat ggaaggtatt ataaccatgt   1200
catggtgcat atggaaatgt cgaaataact ggatattcga aaacataccg ccaacggtgg   1260
cggcctgcaa ggaaatgttc aagactgaaa tgaactacat ctgctaccaa gttaagctcg   1320
agacaggagc taaaagtaga aactggatac aacactttgt aacatagtga cactcccctt   1380
ttcctttctt ttaccttaga actatacata caatccacat tcaataaaaa tttgtaggta   1440
cgccatacac actaccggaa tccggctctt tgccgagtgt gaggcgcttt gtcgagtgct   1500
ttttgtccag cactcggcaa aaaagtcttt gccatgtgcc gcactcggca aagtcctgct   1560
ctcggtaacg accgcgttta ccgagagcag gactctcgac acagaaatac actcgacaaa   1620
gaaatctttg ccgagagcca aacactcggc gaacggcagc gctcggcaaa gggtcgtcag   1680
ccgccgtcta aagctgacgg tcgttatctt tgtcgagtgc cccctcgtcc gacactcagt   1740
agagcaagct tgccgagtgc catccttgga cactcgataa agtatatttt attttttttt   1800
attttgccaa ccaaactttt tgtggtatgt tcctacacta tgtagatcta catgtaccat   1860
tttggcacaa ttacaaaaat gttttctata actattagat ttagttcgtt tatttgaatt   1920
tcttcggaaa attcacatat gaactgcaag tcactcgaaa catgaaaaac cgtgcatgca   1980
aaataaatga tatgcatgtt atctagcaca agttacgacc gaattcagaa gcagaccaga   2040
atcttcaagc accatgctca ctaaacatga ccgtgaactt gttatccagt tgtttaaaaa   2100
ttgtataaaa cacaaataaa gtcagaaatt aatgaaactt gtccacatgt catgatatca   2160
tatatagagg ttgtgataaa aatttgataa tgtttcggta aagttgtgac gtactatgtg   2220
tagaaaccta agtgacctac acataaaatc atagagtttc aatgtagttc actcgacaaa   2280
gactttgtca agtgtccgat aaaaagtatt cagcaaagaa gccgttgtcg atttactgtt   2340
cgtcgagatc tctttgccga gtgtcacact aggcaaagtc tttacggagt gtttttcagg   2400
ctttgacact cggcaaagcg ctcgattcca gtagtgacag taatttgcat caaaaatagc   2460
cgagagattt aaaatgagtc aactaataga ccaactaatt attagctatt agtcgttagc   2520
ttctttaatc taagctaaaa ccaactaata gcttatttgt tgaattacaa ttagctcaac   2580
ggaattctct gtttttteta taaaaaaaag ggaaactgcc cctcatttac agcaaactgt   2640
ccgctgcctg tcgtccagat acaatgaacg tacctagtag gaactctttt acacgctcgg   2700
tcgctcgccg cggatcggag tcccaggaac acgacaccac tgtggaacac gacaaagtct   2760
gctcagaggc ggccacaccc tggcgtgcac cgagccggag cccggataag cacggtaagg   2820
agagtacggc gggacgtggc gacccgtgtg tctgctgcca cgcagccttc ctccacgtag   2880
ccgcgcggcc gcgccacgta ccagggcccg gcgctggtat aaatgcgcgc cacctccgct   2940
```

-continued ttagttctgc atacagccaa cccaacacac acccgagcat atcacagtga cagacactac 3000
acgatg 3006

<210> SEQ ID NO 7
<211> LENGTH: 2950
<212> TYPE: DNA
<213> ORGANISM: Zea mays

<400> SEQUENCE: 7
cggtatgaat ttggaaacaa attcagtact tttaaaaaaa tttgttgtag ggagcaaata 60
atacataaaa taatttatgc attattttat tttttatttg taataaatatg cttgaaacga 120 taattcagta tgcatgttgt gccagtgtac tacacgggcg gggggagggg attgagtggg 180
ccagcgcggt gcgtagggta gatgggctga aattgataac tcaagtccga ctaggttctc 240
tttttatttc ccttcctttt ctattttcct ttcttttaat tttcatgctt tcaaactaaa 300
ttcaaattcg agttttgaat ttcagcttct aaattgtaca ctaaaattat atgataaggt 360 aaccccctact attactttta attttttat tctaccccat attgtttact taggggagaa 420
taattgactt aatcacattc ttcctaggtt tcaattctca atctttcaaa tccacatttt 480
tagatttcta ttttgaattt aaataccagt ttggatttag agttcaattt caaaatacac 540
aaccaaaata ccagcatgaa tgcaaatata ttttatgttt atgtatttac ttttctttta 600
tactttgctc aaaatagtta ttttcatgta tgaaactcaa taagcaagga actcacgtta 660
ttatataacc taataggaat aatttaggta acataattta tcatcctctt gatttaaaag 720
agatatgcct ccagaataag acacatacta aaaataactc taatattgaa taactaaagt 780
cgtacaaatc tctactatta ttcctataaa ataataaaga actagctaca acttctttaa 840
ggcattattc agggtttaca gcttgagagg catgaaccca tcctgtatac tcctggactt 900
ggaagacaaa atgtcaacca aagtgaaagg ttttcttatg gttgctgcta agagatagat 960
tgaacactag atctctccta agacgtcagg gcatgcgttt agactcctac acatgcgaaa 1020
actgcatctt acagttggaa gaaactatat ctcaccactt cctgcggtgt aactttgccc 1080
aaagatgttg gctcactgtt ggaatcactc cgccccgaac tttggatcta acgcttgcag 1140
tgctacatat tagagcaaga ctaacaatgc cgtggagaat ggaaggtatt ataaccatgt 1200
catggtgcat atggaaatgt cgaaataact ggatattcga aaacataccg ccaacggtgg 1260
cggcctgcaa ggaaatgttc aagactgaaa tgaactacat ctgctaccaa gttaagctcg 1320
agacaggagc taaaagtaga aactggatac aacactttgt aacatagtga cactcccctt 1380
ttcctttctt ttaccttaga actatacata caatccacat tcaataaaaa tttgtaggta 1440
cgccatacac actaccggaa tccggctctt tgccgagtgt gaggcgcttt gtcgagtgct 1500
ttttgtccag cactcggcaa aaaagtcttt gccatgtgcc gcactcggca aagtcctgct 1560
ctcggtaacg accgcgttta ccgagagcag gactctcgac acagaaatac actcgacaaa 1620
gaaatctttg ccgagagcca aacactcggc gaacggcagc gctcggcaaa gggtcgtcag 1680
ccgccgtcta aagctgacgg tcgttatctt tgtcgagtgc cccctcgtcc gacactcagt 1740
agagcaagct tgccgagtgc catccttgga cactcgataa agtatatttt attttttttt 1800
attttgccaa ccaaactttt tgtggtatgt tcctacacta tgtagatcta catgtaccat 1860
tttggcacaa ttacaaaaat gttttctata actattagat ttagttcgtt tatttgaatt 1920
tcttcggaaa attcacatat gaactgcaag tcactcgaaa catgaaaaac cgtgcatgca 1980
aaataaatga tatgcatgtt atctagcaca agttacgacc gaattcagaa gcagaccaga 2040
atcttcaagc accatgctca ctaaacatga ccgtgaactt gttatccagt tgtttaaaaa 2100
ttgtataaaa cacaaataaa gtcagaaatt aatgaaactt gtccacatgt catgatatca 2160
tatatagagg ttgtgataaa aatttgataa tgtttcggta aagttgtgac gtactatgtg 2220
tagaaaccta agtgacctac acataaaatc atagagtttc aatgtagttc actcgacaaa 2280
gactttgtca agtgtccgat aaaaagtatt cagcaaagaa gccgttgtcg atttactgtt 2340
cgtcgagatc tctttgccga gtgtcacact aggcaaagtc tttacggagt gtttttcagg 2400
ctttgacact cggcaaagcg ctcgattcca gtagtgacag taatttgcat caaaaatagc 2460
cgagagattt aaaatgagtc aactaataga ccaactaatt attagctatt agtcgttagc 2520
ttctttaatc taagctaaaa ccaactaata gcttatttgt tgaattacaa ttagctcaac 2580
ggaattctct gtttttcta taaaaaaaag ggaaactgcc cctcatttac agcaaactgt 2640
ccgctgcctg tcgtccagat acaatgaacg tacctagtag gaactctttt acacgctcgg 2700
tcgctcgccg cggatcggag tcccaggaac acgacaccac tgtggaacac gacaaagtct 2760
gctcagaggc ggccacaccc tggcgtgcac cgagccggag cccggataag cacggtaagg 2820
agagtacggc gggacgtggc gacccgtgtg tctgctgcca cgcagccttc ctccacgtag 2880
ccgcgcggcc gcgccacgta ccagggcccg gcgctggtat aaatgcgcgc cacctccgct 2940
ttagttctgc 2950

<210> SEQ ID NO 8
<211> LENGTH: 53
<212> TYPE: DNA
<213> ORGANISM: Zea mays

<400> SEQUENCE: 8
atacagccaa cccaacacac acccgagcat atcacagtga cagacactac acg 53

<210> SEQ ID NO 9
<211> LENGTH: 7262
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9
ggcgcgccgg tatgaatttg gaaacaaatt cagtactttt aaaaaaattt gttgtaggga 60
gcaaataata cataaaataa tttatgcatt attttatttt ttatttgtaa taatatgctt 120
gaaacgataa ttcagtatgc atgttgtgcc agtgtactac acgggcgggg ggaggggatt 180
gagtgggcca gcgcggtgcg tagggtagat gggctgaaat tgataactca agtccgacta 240
ggttctcttt ttatttccct tccttttcta ttttcctttc ttttaatttt catgctttca 300
aactaaattc aaattcgagt tttgaatttc agcttctaaa ttgtacacta aaattatatg 360
ataaggtaac ccctactatt acttttaatt tttttattct accccatatt gtttacttag 420
gggagaataa ttgacttaat cacattcttc ctaggtttca attctcaatc tttcaaatcc 480
acatttttag atttctattt tgaatttaaa taccagtttg gatttagagt tcaatttcaa 540
aatacacaac caaaatacca gcatgaatgc aaatatattt tatgtttatg tatttacttt 600
tcttttatac tttgctcaaa atagttattt tcatgtatga aactcaataa gcaaggaact 660
cacgttatta tataacctaa taggaataat ttaggtaaca taatttatca tcctcttgat 720
ttaaaagaga tatgcctcca gaataagaca catactaaaa ataactctaa tattgaataa 780

-continued

```
ctaaagtcgt acaaatctct actattattc ctataaaata ataaagaact agctacaact    840
tctttaaggc attattcagg gtttacagct tgagaggcat gaacccatcc tgtatactcc    900
tggacttgga agacaaaatg tcaaccaaag tgaaaggttt tcttatggtt gctgctaaga    960
gatagattga acactagatc tctcctaaga cgtcagggca tgcgtttaga ctcctacaca   1020
tgcgaaaact gcatcttaca gttggaagaa actatatctc accacttcct gcggtgtaac   1080
tttgcccaaa gatgttggct cactgttgga atcactccgc cccgaacttt ggatctaacg   1140
cttgcagtgc tacatattag agcaagacta acaatgccgt ggagaatgga aggtattata   1200
accatgtcat ggtgcatatg gaaatgtcga aataactgga tattcgaaaa cataccgcca   1260
acggtggcgg cctgcaagga aatgttcaag actgaaatga actacatctg ctaccaagtt   1320
aagctcgaga caggagctaa aagtagaaac tggatacaac actttgtaac atagtgacac   1380
tcccctttc ctttctttta ccttagaact atacatacaa tccacattca ataaaaattt   1440
gtaggtacgc catacacact accggaatcc ggctctttgc cgagtgtgag gcgctttgtc   1500
gagtgctttt tgtccagcac tcggcaaaaa agtctttgcc atgtgccgca ctcggcaaag   1560
tcctgctctc ggtaacgacc gcgtttaccg agagcaggac tctcgacaca gaaatacact   1620
cgacaaagaa atctttgccg agagccaaac actcggcgaa cggcagcgct cggcaaaggg   1680
tcgtcagccg ccgtctaaag ctgacggtcg ttatctttgt cgagtgcccc ctcgtccgac   1740
actcagtaga gcacgcgccg gtatgaattt ggaaacaaat tcagtacttt taaaaaaatt   1800
tgttgtaggg agcaaataat acataaaata atttatgcat tattttattt tttatttgta   1860
ataaatatgct tgaaacgata attcagtatg catgttgtgc cagtgtacta cacgggcggg   1920
gggaggggat tgagtgggcc agcgcggtgc gtagggtaga tgggctgaaa ttgataactc   1980
aagtccgact aggttctctt tttatttccc ttccttttct attttccttt cttttaattt   2040
tcatgctttc aaactaaatt caaattcgag ttttgaattt cagcttctaa attgtacact   2100
aaaattatat gataaggtaa cccctactat tacttttaat ttttttattc taccccatat   2160
tgtttactta ggggagaata attgacttaa tcacattctt cctaggtttc aattctcaat   2220
ctttcaaatc cacattttta gatttctatt ttgaatttaa ataccagttt ggatttagag   2280
ttcaatttca aaatacacaa ccaaaatacc agcatgaatg caaatatatt ttatgtttat   2340
gtatttactt ttcttttata ctttgctcaa aatagttatt ttcatgtatg aaactcaata   2400
agcaaggaac tcacgttatt atataaccta ataggaataa tttaggtaac ataatttatc   2460
atcctcttga tttaaaagag atatgcctcc agaataagac acatactaaa aataactcta   2520
atattgaata actaaagtcg tacaaatctc tactattatt cctataaaat aataaagaac   2580
tagctacaac ttctttaagg cattattcag ggtttacagc ttgagaggca tgaacccatc   2640
ctgtatactc ctggacttgg aagacaaaat gtcaaccaaa gtgaaaggtt ttcttatggt   2700
tgctgctaag agatagattg aacactagat ctctcctaag acgtcagggc atgcgtttag   2760
actcctacac atgcgaaaac tgcatcttac agttggaaga aactatatct caccacttcc   2820
tgcggtgtaa ctttgcccaa agatgttggc tcactgttgg aatcactccg ccccgaactt   2880
tggatctaac gcttgcagtg ctacatatta gagcaagact aacaatgccg tggagaatgg   2940
aaggtattat aaccatgtca tggtgcatat ggaaatgtcg aaataactgg atattcgaaa   3000
acataccgcc aacggtggcg gcctgcaagg aaatgttcaa gactgaaatg aactacatct   3060
gctaccaagt taagctcgag acaggagcta aaagtagaaa ctggatacaa cactttgtaa   3120
```

```
catagtgaca ctccccttt cctttctttt accttagaac tatacataca atccacattc   3180
aataaaaatt tgtaggtacg ccatacacac taccggaatc cggctctttg ccgagtgtga   3240
ggcgctttgt cgagtgcttt ttgtccagca ctcggcaaaa aagtctttgc catgtgccgc   3300
actcggcaaa gtcctgctct cggtaacgac cgcgtttacc gagagcagga ctctcgacac   3360
agaaatacac tcgacaaaga aatctttgcc gagagccaaa cactcggcga acggcagcgc   3420
tcggcaaagg gtcgtcagcc gccgtctaaa gctgacggtc gttatctttg tcgagtgccc   3480
cctcgtccga cactcagtag agcacgcgcc ggtatgaatt tggaaacaaa ttcagtactt   3540
ttaaaaaaat ttgttgtagg gagcaaataa tacataaaat aatttatgca ttattttatt   3600
ttttatttgt aataatatgc ttgaaacgat aattcagtat gcatgttgtg ccagtgtact   3660
acacgggcgg ggggagggga ttgagtgggc cagcgcggtg cgtagggtag atgggctgaa   3720
attgataact caagtccgac taggttctct ttttatttcc cttccttttc tattttcctt   3780
tcttttaatt ttcatgcttt caaactaaat tcaaattcga gttttgaatt tcagcttcta   3840
aattgtacac taaaattata tgataaggta accccctacta ttacttttaa ttttttttatt   3900
ctaccccata ttgtttactt aggggagaat aattgactta atcacattct tcctaggttt   3960
caattctcaa tctttcaaat ccacattttt agatttctat tttgaattta aataccagtt   4020
tggatttaga gttcaatttc aaaatacaca accaaaatac cagcatgaat gcaaatatat   4080
tttatgttta tgtatttact tttcttttat actttgctca aaatagttat tttcatgtat   4140
gaaactcaat aagcaaggaa ctcacgttat tatataacct aataggaata atttaggtaa   4200
cataatttat catcctcttg atttaaaaga gatatgcctc cagaataaga cacatactaa   4260
aaataactct aatattgaat aactaaagtc gtacaaatct ctactattat tcctataaaa   4320
taataaagaa ctagctacaa cttctttaag gcattattca gggtttacag cttgagaggc   4380
atgaacccat cctgtatact cctggacttg gaagacaaaa tgtcaaccaa agtgaaaggt   4440
tttcttatgg ttgctgctaa gagatagatt gaacactaga tctctcctaa gacgtcaggg   4500
catgcgttta gactcctaca catgcgaaaa ctgcatctta cagttggaag aaactatatc   4560
tcaccacttc ctgcggtgta actttgccca aagatgttgg ctcactgttg gaatcactcc   4620
gccccgaact ttggatctaa cgcttgcagt gctacatatt agagcaagac taacaatgcc   4680
gtggagaatg gaaggtatta taaccatgtc atggtgcata tggaaatgtc gaaataactg   4740
gatattcgaa aacataccgc caacggtggc ggcctgcaag gaaatgttca agactgaaat   4800
gaactacatc tgctaccaag ttaagctcga gacaggagct aaaagtagaa actggataca   4860
acactttgta acatagtgac actccccttt tcctttcttt taccttagaa ctatacatac   4920
aatccacatt caataaaaat ttgtaggtac gccatacaca ctaccggaat ccggctcttt   4980
gccgagtgtg aggcgctttg tcgagtgctt tttgtccagc actcggcaaa aaagtctttg   5040
ccatgtgccg cactcggcaa agtcctgctc tcggtaacga ccgcgtttac cgagagcagg   5100
actctcgaca cagaaataca ctcgacaaag aaatctttgc cgagagccaa acactcggcg   5160
aacggcagcg ctcggcaaag ggtcgtcagc cgccgtctaa agctgacggt cgttatcttt   5220
gtcgagtgcc ccctcgtccg acactcagta gagcaagctt gccgagtgcc atccttggac   5280
actcgataaa gtatatttta ttttttttta ttttgccaac caaacttttt gtggtatgtt   5340
cctacactat gtagatctac atgtaccatt ttggcacaat tacaaaaatg ttttctataa   5400
ctattagatt tagttcgttt atttgaattt cttcggaaaa ttcacatatg aactgcaagt   5460
cactcgaaac atgaaaaacc gtgcatgcaa aataaatgat atgcatgtta tctagcacaa   5520
```

```
gttacgaccg aattcagaag cagaccagaa tcttcaagca ccatgctcac taaacatgac   5580
cgtgaacttg ttatccagtt gtttaaaaat tgtataaaac acaaataaag tcagaaatta   5640
atgaaacttg tccacatgtc atgatatcat atatagaggt tgtgataaaa atttgataat   5700
gtttcggtaa agttgtgacg tactatgtgt agaaacctaa gtgacctaca cataaaatca   5760
tagagtttca atgtagttca ctcgacaaag actttgtcaa gtgtccgata aaaagtattc   5820
agcaaagaag ccgttgtcga tttactgttc gtcgagatct ctttgccgag tgtcacacta   5880
ggcaaagtct ttacggagtg tttttcaggc tttgacactc ggcaaagcgc tcgattccag   5940
tagtgacagt aatttgcatc aaaaatagcc gagagattta aaatgagtca actaatagac   6000
caactaatta ttagctatta gtcgttagct tctttaatct aagctaaaac caactaatag   6060
cttatttgtt gaattacaat tagctcaacg gaattctctg ttttttctat aaaaaaaagg   6120
gaaactgccc ctcatttaca gcaaactgtc cgctgcctgt cgtccagata caatgaacgt   6180
acctagtagg aactctttta cacgctcggt cgctcgccgc ggatcggagt cccaggaaca   6240
cgacaccact gtggaacacg acaaagtctg ctcagaggcg gccacaccct ggcgtgcacc   6300
gagccggagc ccggataagc acggtaagga gagtacggcg ggacgtggcg acccgtgtgt   6360
ctgctgccac gcagccttcc tccacgtagc cgcgcggccg cgccacgtac cagggcccgg   6420
cgctggtata aatgcgcgcc acctccgctt tagttctgca tacagccaac ccaacacaca   6480
cccgagcata tcacagtgac agacactaca ccatggccaa caagcacctg agcctctccc   6540
tcttcctcgt gctcctcggc ctctccgcct ccctcgccag cggcgagtcc accacctccg   6600
gcttcctcgg cccgctcctc gtgctccagg ccggcttctc cctcctcacc cgcatcctca   6660
ccatcccgca gtccctcgac tcctggtgga cctccctcaa cttcctcggc ggcgccccga   6720
cctgcccggg ccagaacctc cagtccccga cctccaacca ctccccgacc tcctgcccgc   6780
ccacctgccc gggctaccgc tggatgtgcc tccgccgctt catcatcttc ctcttcatcc   6840
tcctgctctg cctcatcttc ctcctcgtgc tcgtggacta ccagggcatg ctcccggtgt   6900
gcccgctcct cccgggcacc tccacgacct ccaccggccc gtgcaagacc tgcaccatcc   6960
cggcccaggg cacctccatg ttcccgtcct gctgctgcac caagccgtcc gacggcaact   7020
gcgcctgcat cccgatcccg tcctcctggg ccttcgcccg cttcctctgg gagtgggcct   7080
ccgtgcgctt ctcctggctc tccctcctcg tgccgttcgt gcagtggttc gtgggcctct   7140
ccccgaccgt gtggctctcc gtgatctgga tgatgtggta ctggggcccg tccctctaca   7200
acatcctctc cccgttcctc ccgctcctcc cgatcttctt ctgcctctgg gtgtacatct   7260
ga                                                                  7262
```

<210> SEQ ID NO 10
<211> LENGTH: 1745
<212> TYPE: DNA
<213> ORGANISM: Zea mays

<400> SEQUENCE: 10

```
cggtatgaat ttggaaacaa attcagtact tttaaaaaaa tttgttgtag ggagcaaata     60
atacataaaa taatttatgc attattttat tttttatttg taataatatg cttgaaacga    120
taattcagta tgcatgttgt gccagtgtac tacacgggcg gggggagggg attgagtggg    180
ccagcgcggt gcgtagggta gatgggctga aattgataac tcaagtccga ctaggttctc    240
tttttatttc ccttcctttt ctattttcct ttcttttaat tttcatgctt tcaaactaaa    300
```

```
ttcaaattcg agttttgaat ttcagcttct aaattgtaca ctaaaattat atgataaggt    360
aacccctact attactttta attttttat tctaccccat attgtttact taggggagaa    420
taattgactt aatcacattc ttcctaggtt tcaattctca atctttcaaa tccacatttt    480
tagatttcta ttttgaattt aaataccagt ttggatttag agttcaattt caaaatacac    540
aaccaaaata ccagcatgaa tgcaaatata ttttatgttt atgtatttac ttttctttta    600
tactttgctc aaaatagtta ttttcatgta tgaaactcaa taagcaagga actcacgtta    660
ttatataacc taataggaat aatttaggta acataattta tcatcctctt gatttaaaag    720
agatatgcct ccagaataag acacatacta aaaataactc taatattgaa taactaaagt    780
cgtacaaatc tctactatta ttcctataaa ataataaaga actagctaca acttctttaa    840
ggcattattc agggtttaca gcttgagagg catgaaccca tcctgtatac tcctggactt    900
ggaagacaaa atgtcaacca aagtgaaagg ttttcttatg gttgctgcta agagatagat    960
tgaacactag atctctccta agacgtcagg gcatgcgttt agactcctac acatgcgaaa   1020
actgcatctt acagttggaa gaaactatat ctcaccactt cctgcggtgt aactttgccc   1080
aaagatgttg gctcactgtt ggaatcactc cgccccgaac tttggatcta acgcttgcag   1140
tgctacatat tagagcaaga ctaacaatgc cgtggagaat ggaaggtatt ataaccatgt   1200
catggtgcat atggaaatgt cgaaataact ggatattcga aaacataccg ccaacggtgg   1260
cggcctgcaa ggaaatgttc aagactgaaa tgaactacat ctgctaccaa gttaagctcg   1320
agacaggagc taaaagtaga aactggatac aacactttgt aacatagtga cactcccctt   1380
ttcctttctt ttaccttaga actatacata caatccacat tcaataaaaa tttgtaggta   1440
cgccatacac actaccggaa tccggctctt tgccgagtgt gaggcgcttt gtcgagtgct   1500
ttttgtccag cactcggcaa aaaagtcttt gccatgtgcc gcactcggca aagtcctgct   1560
ctcggtaacg accgcgttta ccgagagcag gactctcgac acagaaatac actcgacaaa   1620
gaaatctttg ccgagagcca aacactcggc gaacggcagc gctcggcaaa gggtcgtcag   1680
ccgccgtcta aagctgacgg tcgttatctt tgtcgagtgc cccctcgtcc gacactcagt   1740
agagc                                                               1745

<210> SEQ ID NO 11
<211> LENGTH: 3006
<212> TYPE: DNA
<213> ORGANISM: Zea mays
<400> SEQUENCE: 11
cggtatgaat ttggaaacaa attcagtact tttaaaaaaa tttgttgtag ggagcaaata     60
atacataaaa taatttatgc attattttat tttttatttg taataatatg cttgaaacga    120
taattcagta tgcatgttgt gccagtgtac tacacgggcg gggggagggg attgagtggg    180
ccagcgcggt gcgtagggta gatgggctga aattgataac tcaagtccga ctaggttctc    240
tttttatttc ccttcctttt ctattttcct ttcttttaat tttcatgctt tcaaactaaa    300
ttcaaattcg agttttgaat ttcagcttct aaattgtaca ctaaaattat atgataaggt    360
aacccctact attactttta attttttat tctaccccat attgtttact taggggagaa    420
taattgactt aatcacattc ttcctaggtt tcaattctca atctttcaaa tccacatttt    480
tagatttcta ttttgaattt aaataccagt ttggatttag agttcaattt caaaatacac    540
aaccaaaata ccagcatgaa tgcaaatata ttttatgttt atgtatttac ttttctttta    600
tactttgctc aaaatagtta ttttcatgta tgaaactcaa taagcaagga actcacgtta    660
```

-continued

```
ttatataacc taataggaat aatttaggta acataattta tcatcctctt gatttaaaag    720
agatatgcct ccagaataag acacatacta aaaataactc taatattgaa taactaaagt    780
cgtacaaatc tctactatta ttcctataaa ataataaaga actagctaca acttctttaa    840
ggcattattc agggtttaca gcttgagagg catgaaccca tcctgtatac tcctggactt    900
ggaagacaaa atgtcaacca aagtgaaagg ttttcttatg gttgctgcta agagatagat    960
tgaacactag atctctccta agacgtcagg gcatgcgttt agactcctac acatgcgaaa   1020
actgcatctt acagttggaa gaaactatat ctcaccactt cctgcggtgt aactttgccc   1080
aaagatgttg gctcactgtt ggaatcactc cgcccccgaac tttggatcta acgcttgcag   1140
tgctacatat tagagcaaga ctaacaatgc cgtggagaat ggaaggtatt ataaccatgt   1200
catggtgcat atggaaatgt cgaaataact ggatattcga aaacataccg ccaacggtgg   1260
cggcctgcaa ggaaatgttc aagactgaaa tgaactacat ctgctaccaa gttaagctcg   1320
agacaggagc taaaagtaga aactggatac aacactttgt aacatagtga cactcccctt   1380
ttcctttctt ttaccttaga actatacata caatccacat tcaataaaaa tttgtaggta   1440
cgccatacac actaccggaa tccggctctt tgccgagtgt gaggcgcttt gtcgagtgct   1500
ttttgtccag cactcggcaa aaaagtcttt gccatgtgcc gcactcggca aagtcctgct   1560
ctcggtaacg accgcgttta ccgagagcag gactctcgac acagaaatac actcgacaaa   1620
gaaatctttg ccgagagcca aacactcggc gaacggcagc gctcggcaaa gggtcgtcag   1680
ccgccgtcta aagctgacgg tcgttatctt tgtcgagtgc cccctcgtcc gacactcagt   1740
agagcaagct tgccgagtgc catccttgga cactcgataa agtatatttt attttttttt   1800
attttgccaa ccaaactttt tgtggtatgt tcctacacta tgtagatcta catgtaccat   1860
tttggcacaa ttacaaaaat gttttctata actattagat ttagttcgtt tatttgaatt   1920
tcttcggaaa attcacatat gaactgcaag tcactcgaaa catgaaaaac cgtgcatgca   1980
aaataaatga tatgcatgtt atctagcaca agttacgacc gaattcagaa gcagaccaga   2040
atcttcaagc accatgctca ctaaacatga ccgtgaactt gttatccagt tgtttaaaaa   2100
ttgtataaaa cacaaataaa gtcagaaatt aatgaaactt gtccacatgt catgatatca   2160
tatatagagg ttgtgataaa aatttgataa tgtttcggta aagttgtgac gtactatgtg   2220
tagaaaccta agtgacctac acataaaatc atagagtttc aatgtagttc actcgacaaa   2280
gactttgtca agtgtccgat aaaaagtatt cagcaaagaa gccgttgtcg atttactgtt   2340
cgtcgagatc tctttgccga gtgtcacact aggcaaagtc tttacggagt gtttttcagg   2400
ctttgacact cggcaaagcg ctcgattcca gtagtgacag taatttgcat caaaaatagc   2460
cgagagattt aaaatgagtc aactaataga ccaactaatt attagctatt agtcgttagc   2520
ttctttaatc taagctaaaa ccaactaata gcttatttgt tgaattacaa ttagctcaac   2580
ggaattctct gtttttttcta taaaaaaaag ggaaactgcc cctcatttac agcaaactgt   2640
ccgctgcctg tcgtccagat acaatgaacg tacctagtag gaactctttt acacgctcgg   2700
tcgctcgccg cggatcggag tcccaggaac acgacaccac tgtggaacac gacaaagtct   2760
gctcagaggc ggccacaccc tggcgtgcac cgagccggag cccggataag cacggtaagg   2820
agagtacggc gggacgtggc gacccgtgtg tctgctgcca cgcagccttc ctccacgtag   2880
ccgcgcggcc gcgccacgta ccagggcccg gcgctggtat aaatgcgcgc cacctccgct   2940
ttagttctgc atacagccaa cccaacacac acccgagcat atcacagtga cagacactac   3000
```

-continued accatg 3006

<210> SEQ ID NO 12
<211> LENGTH: 5935
<212> TYPE: DNA
<213> ORGANISM: Zea mays

<400> SEQUENCE: 12
tagagttcaa tttcaaaata cacaaccaaa ataccagcat gaatgcaaat atattttatg 60
tttatgtatt tacttttctt ttatactttg ctcaaaatag ttattttcat gtatgaaact 120
caataagcaa ggaactcacg ttattatata acctaatagg aataatttag gtaacataat 180
ttatcatcct cttgatttaa aagagatatg cctccagaat aagacacata ctaaaaataa 240
ctctaatatt gaataactaa agtcgtacaa atctctacta ttattcctat aaaataataa 300
agaactagct acaacttctt taaggcatta ttcagggttt acagcttgag aggcatgaac 360
ccatcctgta tactcctgga cttggaagac aaaatgtcaa ccaaagtgaa aggttttctt 420
atggttgctg ctaagagata gattgaacac tagatctctc ctaagacgtc agggcatgcg 480
tttagactcc tacacatgcg aaaactgcat cttacagttg gaagaaacta tatctcacca 540
cttcctgcgg tgtaactttg cccaaagatg ttggctcact gttggaatca ctccgccccg 600
aactttggat ctaacgcttg cagtgctaca tattagagca agactaacaa tgccgtggag 660
aatggaaggt attataacca tgtcatggtg catatggaaa tgtcgaaata actggatatt 720
cgaaaacata ccgccaacgg tggcggcctg caaggaaatg ttcaagactg aaatgaacta 780
catctgctac caagttaagc tcgagacagg agctaaaagt agaaactgga tacaacactt 840
tgtaacatag tgacactccc cttttccttt cttttacctt agaactatac atacaatcca 900
cattcaataa aaatttgtag gtacgccata cacactaccg gaatccggct ctttgccgag 960
tgtgaggcgc tttgtcgagt gctttttgtc cagcactcgg caaaaaagtc tttgccatgt 1020
gccgcactcg gcaaagtcct gctctcggta acgaccgcgt ttaccgagag caggactctc 1080
gacacagaaa tacactcgac aaagaaatct ttgccgagag ccaaacactc ggcgaacggc 1140
agcgctcggc aaagggtcgt cagccgccgt ctaaagctga cggtcgttat ctttgtcgag 1200
tgccccctcg tccgacactc agtagagcac gcgccggtat gaatttggaa acaaattcag 1260
tacttttaaa aaaatttgtt gtagggagca aataatacat aaaataattt atgcattatt 1320 ttattttta tttgtaataa tatgcttgaa acgataattc agtatgcatg ttgtgccagt 1380
gtactacacg ggcgggggga ggggattgag tgggccagcg cggtgcgtag ggtagatggg 1440
ctgaaattga taactcaagt ccgactaggt tctcttttta tttcccttcc ttttctattt 1500
tcctttcttt taattttcat gctttcaaac taaattcaaa ttcgagtttt gaatttcagc 1560
ttctaaattg tacactaaaa ttatatgata aggtaacccc tactattact tttaattttt 1620
ttattctacc ccatattgtt tacttagggg agaataattg acttaatcac attcttccta 1680
ggtttcaatt ctcaatcttt caaatccaca tttttagatt tctattttga atttaaatac 1740
cagtttggat ttagagttca atttcaaaat acacaaccaa aataccagca tgaatgcaaa 1800
tatattttat gtttatgtat ttacttttct tttatacttt gctcaaaata gttattttca 1860
tgtatgaaac tcaataagca aggaactcac gttattatat aacctaatag gaataattta 1920
ggtaacataa tttatcatcc tcttgattta aaagagatat gcctccagaa taagacacat 1980
actaaaaata actctaatat tgaataacta aagtcgtaca aatctctact attattccta 2040
taaaataata aagaactagc tacaacttct ttaaggcatt attcagggtt tacagcttga 2100

-continued

```
gaggcatgaa cccatcctgt atactcctgg acttggaaga caaaatgtca accaaagtga   2160
aaggttttct tatggttgct gctaagagat agattgaaca ctagatctct cctaagacgt   2220
cagggcatgc gtttagactc ctacacatgc gaaaactgca tcttacagtt ggaagaaact   2280
atatctcacc acttcctgcg gtgtaacttt gcccaaagat gttggctcac tgttggaatc   2340
actccgcccc gaactttgga tctaacgctt gcagtgctac atattagagc aagactaaca   2400
atgccgtgga gaatggaagg tattataacc atgtcatggt gcatatggaa atgtcgaaat   2460
aactggatat tcgaaaacat accgccaacg gtggcggcct gcaaggaaat gttcaagact   2520
gaaatgaact acatctgcta ccaagttaag ctcgagacag gagctaaaag tagaaactgg   2580
atacaacact ttgtaacata gtgacactcc ccttttcctt tcttttacct tagaactata   2640
catacaatcc acattcaata aaaatttgta ggtacgccat acacactacc ggaatccggc   2700
tctttgccga gtgtgaggcg ctttgtcgag tgctttttgt ccagcactcg gcaaaaaagt   2760
ctttgccatg tgccgcactc ggcaaagtcc tgctctcggt aacgaccgcg tttaccgaga   2820
gcaggactct cgacacagaa atacactcga caaagaaatc tttgccgaga gccaaacact   2880
cggcgaacgg cagcgctcgg caaagggtcg tcagccgccg tctaaagctg acggtcgtta   2940
tctttgtcga gtgccccctc gtccgacact cagtagagca cgcgccggta tgaatttgga   3000
aacaaattca gtacttttaa aaaaatttgt tgtagggagc aaataataca taaaataatt   3060
tatgcattat tttatttttt atttgtaata atatgcttga aacgataatt cagtatgcat   3120
gttgtgccag tgtactacac gggcgggggg aggggattga gtgggccagc gcggtgcgta   3180
gggtagatgg gctgaaattg ataactcaag tccgactagg ttctcttttt atttcccttc   3240
cttttctatt ttcctttctt ttaattttca tgctttcaaa ctaaattcaa attcgagttt   3300
tgaatttcag cttctaaatt gtacactaaa attatatgat aaggtaaccc ctactattac   3360
ttttaatttt tttattctac cccatattgt ttacttaggg gagaataatt gacttaatca   3420
cattcttcct aggtttcaat tctcaatctt tcaaatccac atttttagat ttctattttg   3480
aatttaaata ccagtttgga tttagagttc aatttcaaaa tacacaacca aaataccagc   3540
atgaatgcaa atatatttta tgtttatgta tttacttttc ttttatactt tgctcaaaat   3600
agttattttc atgtatgaaa ctcaataagc aaggaactca cgttattata taacctaata   3660
ggaataattt aggtaacata atttatcatc ctcttgattt aaaagagata tgcctccaga   3720
ataagacaca tactaaaaat aactctaata ttgaataact aaagtcgtac aaatctctac   3780
tattattcct ataaaataat aaagaactag ctacaacttc tttaaggcat tattcagggt   3840
ttacagcttg agaggcatga acccatcctg tatactcctg gacttggaag acaaaatgtc   3900
aaccaaagtg aaaggttttc ttatggttgc tgctaagaga tagattgaac actagatctc   3960
tcctaagacg tcagggcatg cgtttagact cctacacatg cgaaaactgc atcttacagt   4020
tggaagaaac tatatctcac cacttcctgc ggtgtaactt tgcccaaaga tgttggctca   4080
ctgttggaat cactccgccc cgaactttgg atctaacgct tgcagtgcta catattagag   4140
caagactaac aatgccgtgg agaatggaag gtattataac catgtcatgg tgcatatgga   4200
aatgtcgaaa taactggata ttcgaaaaca taccgccaac ggtggcggcc tgcaaggaaa   4260
tgttcaagac tgaaatgaac tacatctgct accaagttaa gctcgagaca ggagctaaaa   4320
gtagaaactg gatacaacac tttgtaacat agtgacactc cccttttcct ttcttttacc   4380
ttagaactat acatacaatc cacattcaat aaaaatttgt aggtacgcca tacacactac   4440
```

-continued cggaatccgg ctctttgccg agtgtgaggc gctttgtcga gtgcttttttg tccagcactc 4500 ggcaaaaaag tctttgccat gtgccgcact cggcaaagtc ctgctctcgg taacgaccgc 4560
gtttaccgag agcaggactc tcgacacaga aatacactcg acaaagaaat ctttgccgag 4620
agccaaacac tcggcgaacg gcagcgctcg gcaaagggtc gtcagccgcc gtctaaagct 4680
gacggtcgtt atctttgtcg agtgcccct cgtccgacac tcagtagagc aagcttgccg 4740
agtgccatcc ttggacactc gataaagtat attttatttt tttttatttt gccaaccaaa 4800
ctttttgtgg tatgttccta cactatgtag atctacatgt accattttgg cacaattaca 4860
aaaatgtttt ctataactat tagatttagt tcgtttattt gaatttcttc ggaaaattca 4920
catatgaact gcaagtcact cgaaacatga aaaaccgtgc atgcaaaata aatgatatgc 4980
atgttatcta gcacaagtta cgaccgaatt cagaagcaga ccagaatctt caagcaccat 5040
gctcactaaa catgaccgtg aacttgttat ccagttgttt aaaaattgta taaaacacaa 5100
ataaagtcag aaattaatga aacttgtcca catgtcatga tatcatatat agaggttgtg 5160
ataaaaattt gataatgttt cggtaaagtt gtgacgtact atgtgtagaa acctaagtga 5220
cctacacata aaatcataga gtttcaatgt agttcactcg acaaagactt tgtcaagtgt 5280
ccgataaaaa gtattcagca aagaagccgt tgtcgattta ctgttcgtcg agatctcttt 5340
gccgagtgtc acactaggca aagtctttac ggagtgtttt tcaggctttg acactcggca 5400
aagcgctcga ttccagtagt gacagtaatt tgcatcaaaa atagccgaga gatttaaaat 5460
gagtcaacta atagaccaac taattattag ctattagtcg ttagcttctt taatctaagc 5520
taaaaccaac taatagctta tttgttgaat tacaattagc tcaacggaat tctctgtttt 5580
ttctataaaa aaaagggaaa ctgcccctca tttacagcaa actgtccgct gcctgtcgtc 5640
cagatacaat gaacgtacct agtaggaact cttttacacg ctcggtcgct cgccgcggat 5700
cggagtccca ggaacacgac accactgtgg aacacgacaa agtctgctca gaggcggcca 5760
caccctggcg tgcaccgagc cggagcccgg ataagcacgg taaggagagt acggcgggac 5820
gtggcgaccc gtgtgtctgc tgccacgcag ccttcctcca cgtagccgcg cggccgcgcc 5880
acgtaccagg gcccggcgct ggtataaatg cgcgccacct ccgctttagt tctgc 5935

<210> SEQ ID NO 13
<211> LENGTH: 53
<212> TYPE: DNA
<213> ORGANISM: Zea mays

<400> SEQUENCE: 13
atacagccaa cccaacacac acccgagcat atcacagtga cagacactac acc 53

<210> SEQ ID NO 14
<211> LENGTH: 72
<212> TYPE: DNA
<213> ORGANISM: Hordeum vulgare

<400> SEQUENCE: 14
atggccaaca agcacctgag cctctccctc ttcctcgtgc tcctcggcct ctccgcctcc 60
ctcgccagcg gc 72

<210> SEQ ID NO 15
<211> LENGTH: 678
<212> TYPE: DNA
<213> ORGANISM: Hepatitis B virus

<400> SEQUENCE: 15

-continued gagtccacca cctccggctt cctcggcccg ctcctcgtgc tccaggccgg cttctccctc 60
ctcacccgca tcctcaccat cccgcagtcc ctcgactcct ggtggacctc cctcaacttc 120
ctcggcggcg ccccgacctg cccgggccag aacctccagt ccccgacctc caaccactcc 180
ccgacctcct gcccgcccac ctgcccgggc taccgctgga tgtgcctccg ccgcttcatc 240
atcttcctct tcatcctcct gctctgcctc atcttcctcc tcgtgctcgt ggactaccag 300
ggcatgctcc cggtgtgccc gctcctcccg ggcacctcca cgacctccac cggcccgtgc 360
aagacctgca ccatcccggc ccagggcacc tccatgttcc cgtcctgctg ctgcaccaag 420
ccgtccgacg gcaactgcgc ctgcatcccg atcccgtcct cctgggcctt cgcccgcttc 480
ctctgggagt gggcctccgt gcgcttctcc tggctctccc tcctcgtgcc gttcgtgcag 540
tggttcgtgg gcctctcccc gaccgtgtgg ctctccgtga tctggatgat gtggtactgg 600
ggcccgtccc tctacaacat cctctccccg ttcctcccgc tcctcccgat cttcttctgc 660
ctctgggtgt acatctga 678

<210> SEQ ID NO 16
<211> LENGTH: 13
<212> TYPE: DNA
<213> ORGANISM: Artificial Sequence
<220> FEATURE:
<223> OTHER INFORMATION: Description of Artificial Sequence: Synthetic consensus oligonucleotide

<400> SEQUENCE: 16
tccatgcatg cac 13

<210> SEQ ID NO 17
<211> LENGTH: 11
<212> TYPE: DNA
<213> ORGANISM: Zea mays

<400> SEQUENCE: 17
tttatgcatt a 11

<210> SEQ ID NO 18
<211> LENGTH: 10
<212> TYPE: DNA
<213> ORGANISM: Zea mays

<400> SEQUENCE: 18
tatgcttgaa 10

<210> SEQ ID NO 19
<211> LENGTH: 9
<212> TYPE: DNA
<213> ORGANISM: Zea mays

<400> SEQUENCE: 19 tatgcatgt 9

<210> SEQ ID NO 20
<211> LENGTH: 12
<212> TYPE: DNA
<213> ORGANISM: Zea mays

<400> SEQUENCE: 20
ttcatgcttt ca 12

<210> SEQ ID NO 21
<211> LENGTH: 12
<212> TYPE: DNA
<213> ORGANISM: Zea mays

<400> SEQUENCE: 21
taccagcatg aa 12

<210> SEQ ID NO 22
<211> LENGTH: 10
<212> TYPE: DNA
<213> ORGANISM: Zea mays

<400> SEQUENCE: 22
catgaatgca 10

<210> SEQ ID NO 23
<211> LENGTH: 12
<212> TYPE: DNA
<213> ORGANISM: Zea mays

<400> SEQUENCE: 23
ttcatgtatg aa 12

<210> SEQ ID NO 24
<211> LENGTH: 11
<212> TYPE: DNA
<213> ORGANISM: Zea mays

<400> SEQUENCE: 24
gaggcatgaa c 11

<210> SEQ ID NO 25
<211> LENGTH: 10
<212> TYPE: DNA
<213> ORGANISM: Zea mays

<400> SEQUENCE: 25
catgcgttta 10

<210> SEQ ID NO 26
<211> LENGTH: 10
<212> TYPE: DNA
<213> ORGANISM: Zea mays

<400> SEQUENCE: 26
cctgcaagga 10

<210> SEQ ID NO 27
<211> LENGTH: 7
<212> TYPE: DNA
<213> ORGANISM: Artificial Sequence
<220> FEATURE:
<223> OTHER INFORMATION: Description of Artificial Sequence: Synthetic
rice consensus oligonucleotide

<400> SEQUENCE: 27 acgtgkc 7

<210> SEQ ID NO 28
<211> LENGTH: 8
<212> TYPE: DNA
<213> ORGANISM: Artificial Sequence
<220> FEATURE:
<223> OTHER INFORMATION: Description of Artificial Sequence: Synthetic -continued

```
      arabidopsis consensus oligonucleotide

<400> SEQUENCE: 28

bacgtgkm                                                                8


<210> SEQ ID NO 29
<211> LENGTH: 6
<212> TYPE: DNA
<213> ORGANISM: Arabidopsis sp.

<400> SEQUENCE: 29

cacgtt                                                                  6


<210> SEQ ID NO 30
<211> LENGTH: 6
<212> TYPE: DNA
<213> ORGANISM: Arabidopsis sp.

<400> SEQUENCE: 30

gacgtc                                                                  6


<210> SEQ ID NO 31
<211> LENGTH: 43
<212> TYPE: DNA
<213> ORGANISM: Zea mays

<400> SEQUENCE: 31

ggatccaaca cacacccgag gatatcacag tcgacactac acc                        43
```